(12) United States Patent
Amshey et al.

(10) Patent No.: US 7,781,173 B2
(45) Date of Patent: Aug. 24, 2010

(54) HOMOGENEOUS POPULATIONS OF MOLECULES

(75) Inventors: Joseph W. Amshey, Encinitas, CA (US); Roumen A. Bogoev, San Marcos, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 10/949,471

(22) Filed: Sep. 24, 2004

(65) Prior Publication Data

US 2005/0106605 A1   May 19, 2005

Related U.S. Application Data

(60) Provisional application No. 60/582,209, filed on Jun. 22, 2004, provisional application No. 60/506,410, filed on Sep. 25, 2003.

(51) Int. Cl.
*G01N 33/53* (2006.01)
*C12Q 1/68* (2006.01)

(52) U.S. Cl. .................. 435/7.1; 435/4; 530/345; 530/350; 530/352; 528/480

(58) Field of Classification Search ............ 435/7.1, 435/4; 530/345, 350, 352; 528/480
See application file for complete search history.

(56) References Cited

U.S. PATENT DOCUMENTS

| | | | |
|---|---|---|---|
| 3,485,736 A | 12/1969 | Olof et al. | |
| 3,980,540 A | 9/1976 | Hoefer | |
| 4,107,014 A | 8/1978 | Suzuki et al. | |
| 4,142,960 A | 3/1979 | Hahn et al. | |
| 4,337,131 A | 6/1982 | Vesterberg | |
| 4,339,327 A | 7/1982 | Tyler | |
| 4,560,459 A | 12/1985 | Hoefer | |
| 4,574,040 A | 3/1986 | Delony et al. | |
| 5,139,630 A | 8/1992 | Chen | |
| 5,449,758 A | 9/1995 | Hartley | |
| 5,578,180 A | 11/1996 | Engelhorn et al. | |
| 5,580,788 A | 12/1996 | Kihira et al. | |
| 5,582,702 A | 12/1996 | Cabilly et al. | |
| 5,616,228 A | 4/1997 | Nasu et al. | |
| 5,714,326 A | 2/1998 | Dawson | |
| 5,785,832 A | 7/1998 | Chiari et al. | |
| 5,834,247 A | 11/1998 | Comb et al. | |
| 5,865,974 A | 2/1999 | Cabilly et al. | |
| 5,866,683 A | 2/1999 | Shimura et al. | |
| 5,922,185 A | 7/1999 | Updyke et al. | |
| 5,922,858 A | 7/1999 | Rothschild et al. | |
| 5,986,061 A | 11/1999 | Pestka | |
| 6,043,025 A | 3/2000 | Minden et al. | |
| 6,045,995 A | 4/2000 | Cummins et al. | |
| 6,057,106 A | 5/2000 | Updyke et al. | |
| 6,059,948 A | 5/2000 | Updyke et al. | |
| 6,096,182 A | 8/2000 | Updyke et al. | |
| 6,113,766 A | 9/2000 | Steiner et al. | |
| 6,143,154 A | 11/2000 | Updyke et al. | |
| 6,156,182 A | 12/2000 | Olech et al. | |
| 6,162,338 A | 12/2000 | Updyke et al. | |
| 6,379,516 B1 | 4/2002 | Cabilly et al. | |
| 6,495,017 B1 | 12/2002 | Islam et al. | |
| 6,514,938 B1 | 2/2003 | Gad et al. | |
| 6,533,913 B1 | 3/2003 | Tamura et al. | |
| 6,562,213 B1 | 5/2003 | Cabilly et al. | |
| 6,599,410 B1 | 7/2003 | Steiner et al. | |
| 2002/0115103 A1 | 8/2002 | Gad et al. | |
| 2002/0134680 A1 | 9/2002 | Cabilly et al. | |
| 2002/0155455 A1 | 10/2002 | Tadayoni-Rebek et al. | |
| 2003/0015426 A1 | 1/2003 | Rooney et al. | |
| 2003/0121784 A1 | 7/2003 | Updyke et al. | |
| 2003/0127330 A1 | 7/2003 | Updyke et al. | |
| 2003/0153007 A1 | 8/2003 | Chen | |
| 2003/0157720 A1 | 8/2003 | Li | |
| 2003/0162230 A1 | 8/2003 | Reagan et al. | |
| 2003/0232014 A1* | 12/2003 | Burke et al. | ......... 424/1.69 |
| 2004/0014082 A1 | 1/2004 | Tadayoni-Rebeck et al. | |
| 2004/0110186 A1* | 6/2004 | Aebersold et al. | ............ 435/6 |

FOREIGN PATENT DOCUMENTS

| | | |
|---|---|---|
| EP | 0 087 995 | 8/1989 |
| JP | 03015752 | * 1/1991 |
| WO | WO 95/27197 | 10/1995 |
| WO | WO 96/34276 | 10/1996 |
| WO | WO 97/41070 | 11/1997 |
| WO | WO 98/57161 | 12/1998 |
| WO | WO 99/02566 | 1/1999 |
| WO | WO 99/37813 | 7/1999 |
| WO | WO 01/07920 | 2/2001 |
| WO | WO 02/09220 | 1/2002 |

(Continued)

OTHER PUBLICATIONS

Ugozoli et al, Biotechniques, 1992, 12(2), 187-190.*

(Continued)

*Primary Examiner*—T. D. Wessendorf

(57) ABSTRACT

The invention provides populations of molecules that are prepared as, or treated to become, homogeneous for one or more molecular characteristics. In an aspect, the invention relates to molecular weight standards that may be used to determine the molecular weight or apparent molecular weight of uncharacterized molecules, such as proteins and nucleic acids, as well as in other applications. In one aspect, the molecular weight standards are pre-stained.

2 Claims, 10 Drawing Sheets

FOREIGN PATENT DOCUMENTS

| WO | WO 02/13848 | 2/2002 |
|---|---|---|
| WO | WO 02/18901 | 3/2002 |
| WO | WO 02/071024 | 9/2002 |

OTHER PUBLICATIONS

Champliaud et al, Experimental Cell Research 2000, 259(2) 326-335.*

Ailor et al., "Modifying secretion and post-translational processing in insect cells", Curr Opin Biotechnol 10:142-145, 1999.

Andrews, "Electrophoresis on Agarose and Composite Polyacrylamide-Agarose Gels", Electrophoresis, Clarendon Press, p. 148-177; 1986.

Bates et al., "Autonomous parvovirus LuIII encapsidates equal amounts of plus and minus DNA strands" J Virol. 49:319-324, 1984.

Berkelman, T. and T. Stenstedt, 2-D Electrophoresis using immobilized pH gradients—Principles and Methods, Edition AC; Amersham Biosciences, Freiburg, Germany, 1998.

Botti, P et al., "Native chemical ligation using removable Nα-(1-phenyl-2-mercaptoethyl) auxiliaries", Tetrahedron letter 42:1831-33, Elsevier Science, Ltd., 2001.

Bradbury et al., Peptide Amidation, Trends Biochem Sci 16:112-115, 1991.

Breddam et al., "Amidation of Growth Hormone Releasing Factor (1-29) by Serine Carboxypeptidase Catalysed Transpeptidation", Int J Pept Protein Res 37:153-160, 1991.

Clarke, "Protein isoprenylation and methylation at carboxyl-terminal cysteine residues" Annu. Rev. Biochem. 61:355-386, 1992.

Cottingham et al., "A method for the amidation of recombinant peptides expressed as intein fusion proteins in *Escherichia coli*", Nat Biotechnol 19:974-977 (2001).

Crosier et al., "New insights into the control of cell growth; the role of the Axl family" Pathology 29:131-135, 1997.

Dahlberg et al., "Electrophoretic Characterization of Bacterial Polyribosomes in Agarose-Acrylamide Composite Gels", J Mol Biol. 41:139-147, 1969.

Dimitrov, S.I. and Wolfee, A.P., "Fine Resolution of Histones by Two-Dimensional Polyacrylamide Gel Electrophoresis: Developmental Implications" Meth.: A Companion to Meth. Enzymol. 12:57-61. Academic Press, 1997.

Dolnik, "Capillary zone electrophoresis of proteins", Electrophoresis 18:2353-2361, 1997.

Eipper et al., Peptide Alpha-Amidation, Annu Rev Physiol 50:333-344, 1988.

Fehring, V. et al., "Physical markers for landmarking fluorescently stained gels that facilitate automated spot-picking." Electrophoresis 22:2903-2907, Wiley-VCH Verlag GmbH, Aug. 2001.

Ferguson, "Glycosyl-phosphatidylinositol membrane anchors: the tale of a tail." Biochem. Soc. Trans, 20:243-256, 1992.

Fisher et al., "Role of Molecular Conformation in Determining the Electrophoretic Properties of Polynucleotides in Agarose-Acrylamide Composite Gels", Biochemistry 10:1895-1899, 1971.

Flynn et al., Protein Analysis with the BenchMark(tm) Protein, Focus 19:33-35, 1997.

Fournand et al., "Acyl transfer activity of an amidase from *Rhodococcus* sp. strain R312: formation of a wide range of hydroxamic acids", Applied and Environmental Microbiology 64:2844-2852, 1998.

Geoghegan, F.F. et al., "Dye-Pair Reporter Systems for Protein-Peptide Molecular Interactions," Bioconjugate Chem 11:71-77, American Chemical Society, Dec. 2000.

Geoghegan, K.F. and Stroh, J.G., "Site-Directed Conjugation of Nonpeptide Groups to Peptides and Proteins via Periodate Oxidation of a 2-Amino Alcohol. Application to Modification at N-Terminal Serine." Bioconjugate Chem 3:138-146. American Chemical Society, 1992.

Grand, "Acylation of viral and eukaryotic proteins" Biochem J 258:625-638, 1989.

Guttman et al., "Analytical and micropreparative ultrahigh resolution of oligonucleotides by polyacrylamide gel high-performance capillary electrophoresis", Anal. Chem. 62:137-141, 1990.

Han et al., "Post-translational chemical modification(s) of proteins", Int J Biochem 24:19-28, 1992.

Han et al., "Post-Translational Chemical Modifications of Proteins—III. Current Developments in Analytical Procedures of Identification and Quantitation of Post-Translational Chemically Modified Amino Acid(s) and Its Derivatives", Int J Biochem 25:957-970, 1993.

Hjertñï, J. "High-performance electrophoresis: the electrophoretic counterpart of high-performance liquid chromatography", J. Chromatogr. A 270:1-6, 1983.

Horowitz et al., "Electrophoresis of Proteins and Nucleic Acids on Acrylamide-Agarose Gels Lacking Covalent Cross-Linkings", Anal. Biochem. 143:333-340, 1984.

Isono et al., "Lack of ribosomal protein S1 in *Bacillus stearothermophilus*" Proc Natl Acad Sci USA 73:767-770, 1976.

Jaquinod et. al., "Mass Spectrometric Characterization of Post-Translational Modification and Genetic Variation in Human Tetranection", Biol Chem 380:1307-1314, 1999.

Jarvis et al., "Engineering N-glycosylation pathways in the baculovirus-insect cell system" (review), Curr Opin Biotechnol 9:528-533, 1998.

Jimenez et al., "Bromocontryphan: post-translational bromination of tryptophan", Biochemistry 36:989-994, 1997.

Jones et al., A Fluorometric Assay for Peptidyl Alpha-Amidation Activity Using High-Performance Liquid Chromatography, Anal Biochem 168:272-279, 1988.

Kaufmann et al., Use of antibodies for detection of phosphorylated proteins separated by two-dimensional gel electrophoresis (review), Proteomics 1:194-199, 2001.

Kobayashi, h. et al., "Evaluation of pH gradient formation of carrier ampholytes with synthesized isoelectric point markers in capillary isolectric focusing" J. Chromatography 772:137-144, Elsevier Science B.V., 1997.

Koishi et al., "Production of Functional Human Selenocysteine-Containing KDRF/Thioredoxin Reductase in *E. coli*", J. Biochem. 127:977-983, 2000.

Kostich et al., Human Members of the Eukaryotic Protein Kinase Family, Genome Biology 3: research0043.1-0043.12, 2002.

Kouach et al., "Application of Electrospray and Fast Atom Bombardment Mass Spectrometry to the Identification of Post-Translational and Other Chemical Modifications of Proteins 'and Peptides", Biol Mass Spectrom 23:283-294, 1994.

Kuster et al., "Glycosylation Analysis of Gel-Separated Proteins", Proteomics 1:350-361, 2001.

Kuster et al., "Identifying Proteins and Post-Translational Modifications by Mass Spectrometry" (review), Curr Opin Struct Biol. 8:393-400, 1998.

Lee et al., Phosphorylase Phosphatase: New Horizons for an Old Enzyme, Frontiers in Bioscience 4:d270-285, 1999.

Lopez, "Advantages of Carrier Ampholyte IEF", 2-D Proteome Analysis Protocols, Methods Mol Biol. 112:109-110, Humana Press, 1999.

Matsui et al., "Running Preparative Carrier Ampholyte and Immobilized pH Gradient IEF Gels for 2-D", 2-D Proteome Analysis Protocols, Methods Mol Biol. 112:211-219, Humana Press, 1999.

McLachlin et al., "Analysis of phosphorylated proteins and peptides by mass spectrometry" (review), Curr Opin Chem Biol 5:5910-602, 2001.

Merkler, "C-terminal Amidated Peptides: Production by the in Vitro Enzymatic amidation of Glycine-Extended Peptides etc." Enzyme Microb Technol 16:450-458, 1994.

Miner et al., The laminin alpha chains: expression, developmental transitions, and chromosomal locations of alpha1-5, identification of heterotrimeric laminins 8-11, and cloning of a novel alpha3 isoform, J Cell Biol 137:685-701, 1997.

Mironova et al., "Evidence for non-enzymatic glycosylation in *Escherichia coli*", Mol Microbiol 39:1061-1068, 2001.

Nativaeva et al., Post-translational Modifications of Proteins: Acetylcholinesterase as a Model System, Proteomics 1:735-747, 2001.

Nilsson, "Analysis of Protein Glycosylation by Mass Spectrometry", Mol Biotechnol 2:243-280, 1994.

O'Farrell, "High resolution two-dimensional electrophoresis of proteins", J. Biol. Chem. 250:4007-4021, 1975.

Peacock et al., "Molecular Weight Estimation and Separation of Ribonucleic Acid by Electrophoresis in Agarose-Acrylamide Composite Gels," Biochemistry 7:668-674, 1968.

Rando, "Chemical biology of protein isoprenylation/ methylation", Biochim Biophys Acta 1300:5-16, 1996.

Rashid et al., "Electrophoretic Extraction-Concentration of Ribonucleic Acid from Agarose-Acrylamide Composite Gels", Anal Biochem 127:334-339, 1982.

Righetti et al., "Immobilized buffers for isoelectric focusing: From gradient gels to membranes", Electrophoresis 15:1040-1043, 1994.

Righetti et al., "Isoelectric focusing in immobilized pH gradients", Methods Enzymol. 270:235-255, 1996.

Ringborg et al., "Agarose-Acrylamide Composite Gels for Microfractionation of RNA", Nature 220:1037-1039, 1968.

Schuster et al., "Protein expression in yeast; comparison of two expression strategies regarding protein maturation", J Biotechnol 84:237-248, 2000.

Sefton et. al., "The covalent modification of eukaryotic proteins with lipid." J Cell Biol 104:1449-1453, 1987.

Shimura, K and Kasai, K. "Fluorescence-labeled peptides as isoelectric point (pI) markers in capillary isoelectric focusing with fluorescence detection." Electrophoresis 16:1479-1484, Wiley-VCH Verlag Gmbh, 1995.

Shimura, K. et al., "Synthetic oligopeptides as isolectric point markers for capillary isoelectric focusing with ultraviolet absorption detection." Electrophoresis 21:603-610, Wiley-VCH Verlag GmbH, Feb. 2000.

Shimura, K. et. al., "Accuracy in the Determination of Isoelectric Points of Some Proteins and a Peptide by capillary Isoelectric Focusing: Utility of Synthetic Peptides as Isoelectric Point Markers," Anal Chem 72:4747-4757, American Chemical Society, Oct. 2000.

Sickmann et al., "Phosphoamino acid analysis" (review), Proteomics 1:2000-6, 2001.

Simon-Assmann et al., The laminins: role in intestinal morphogenesis and differentiation. Ann N Y Acad Sci. 859:46-64 (Review), 1998.

Slais, K, and Friedl, Z, "Low-molecular-mass p/markers for isoelectric focusing," J. Chromatogr A 661:249-256, Elsevier Science B.V., 1994.

Stadtman, "Selenocysteine" (review), Annu Rev Biochem. 65:83-100, 1996.

Stevenson et al., "The 31-kDa Precursor of Interleukin 1 is Myristoylated on Specific Lysines within the 16-kDa N-Terminal Propiece", Proc. Natl Acad Sci. 90, 7245-7249, 1993.

Teller et al., Interactions between laminin and epithelial cells in intestinal health and disease. Exp. Rev. Mol. Med. Sep. 28, 2001 (available on the internet at <www-ermm.cbcu.cam.ac.uk/01003623h.htm>.

Tolbert. T.J. and Wong. C.-H "Intein-Mediated Synthesis of Proteins Containing Carbohydrates and Other Molecular Probes," J. Am. Chem. Soc. 122:5421-5428. American Chemical Society, May 2000.

Toledo et al., "Methylation of proteins from the translational apparatus: an overview", Arch Biol Med Exp (Santiago) 21:219-229, 1988.

Vosseller et al., "Nucleocytoplasmic O-glycosylation: O-GlcNAc and functional proteomics", Biochimie 83:575-581, 2001.

Yamagata et al., "Mapping of Phosphorylated Proteins on Two-Dimensional Polyacrylamide Gels Using Protein Phosphatase", Proteomics 2:1267-1276, 2002.

Yan et al., "Mass Spectrometric Determination of a Novel Modification of the N-terminus of Histidine-tagged Proteins Expressed in Bacteria", Biochem Biophys Res Commun 259:271-282, 1999.

Yang et al., "In Vitro Amidating Processing of Products Expressed by Gene Engineering", Acta Biochemica et Biophysica Sinica (Shanghai) 32:312-315, 2000.

* cited by examiner

O-linkage to GalNAc

N-linkage to GlcNAc

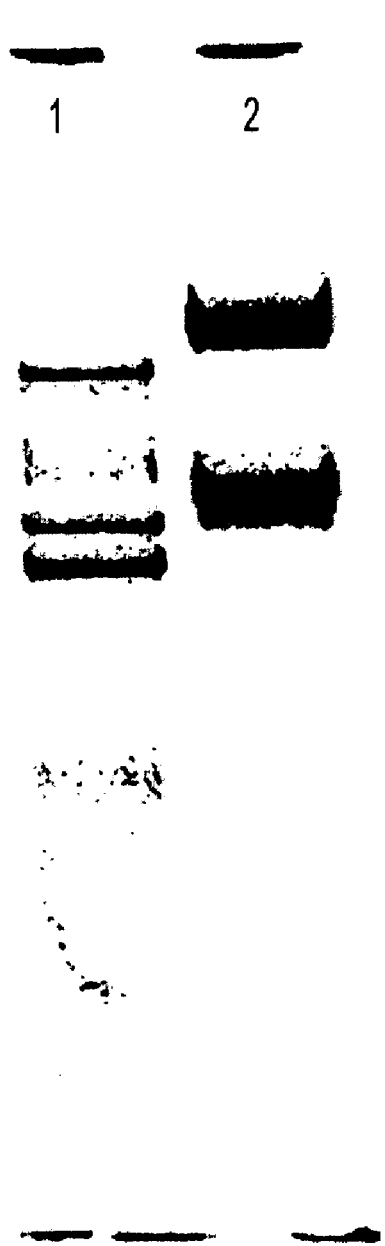
FIG. 4A
FIG. 4B

HOMOGENEOUS POPULATIONS OF MOLECULES

RELATED APPLICATION DATA

This application claims the benefit of priority under 35 U.S.C. §119(e)(1) of U.S. Ser. No. 60/506,410, filed Sep. 25, 2003, entitled "Homogenous Populations of Molecules," and U.S. Ser. No. 60/582,209, filed Jun. 22, 2004 entitled "Homogenous Populations of Molecules," the entire contents of which are incorporated herein by reference.

FIELD OF THE INVENTION

The invention relates to populations of molecules that are prepared as, or treated to become, at least partially homogeneous for one or more molecular characteristics.

BACKGROUND OF THE INVENTION

The term "molecule" is, of course, known in the art. However, it is important to note that the word "molecule" encompasses two concepts. First, a molecule can be the mental picture of a specific molecule as a structure that may be represented by a chemical formula or sequence. Second, the thing that is or comprises a specific molecule, i.e., a population of (about 100 or more) molecules. For example, 18 g of water comprises $6.023 \times 10^{23}$ (Avogadro's number) molecules of $H_2O$.

Although a molecule in the former sense is devoid of other components, a composition comprising an actual population of a given molecule may also comprise other molecules (e.g., contaminants). Populations of molecules are said to be "pure" or to have been "purified" if the number of types or amounts of contaminants have been removed or depleted from compositions comprising populations of specific molecules.

It should be noted that even a pure population of molecules can be heterogeneous with regards to one or more characteristics. For example, as is described in more detail below, a specific protein is glycosylated, i.e., many amino acid residues in the protein have carbohydrates chemically attached thereto. However, in a population of glycosylated proteins, some proteins may be completely glycosylated (all possible glycosylation sites have been glycosylated in all proteins), whereas some may be only partially glycosylated proteins (i.e., only some of the possible glycosylation sites have been glycosylated in all protein and/or not all of proteins are glycosylated to the same extent). In addition, the glycan structures may not be the same on all the glycation sites on the protein.

The invention provides homogeneous, or nearly homogeneous, populations of a molecule that have advantages over heterogeneous populations of the same molecule. Such molecules are useful as, for example, molecular standards.

Compositions and methods useful for the elucidation of the primary structure (i.e., sequence) of an uncharacterized protein or nucleic acid is useful in many applications in fields such as molecular biology, biotechnology, informatics, genomics and proteomics. In order to identify and/or characterize a previously unknown and/or uncharacterized molecule, molecular standards are used.

A "molecular standard" is a molecule that is used to determine a characteristic of an unknown and/or on-test molecule in an assay, such as an analytical method. For example, a molecular standard can be a protein that is used as a molecular weight marker in protein gel electrophoresis, as illustrated in the Examples provided herein.

A "set of standards" are compositions that comprises (i) two or more known molecules differing in at least one detectable characteristic and/or (ii) two or more containers having different concentrations of a known molecule. As a simple example of the latter type of molecular standard, a set of solutions is prepared as a set of serial dilutions of a solution having a known concentration of a known molecule. Although it is customary to have more than one molecule in a molecular weight standard to allow the molecular weight of an unknown molecule to be estimated by interpolation, a single reference standard may be useful for comparison directly with an unknown sample. Differing mobility or other property between the unknown and the standard will indicate lack of identity in the molecular weight or other property being assessed.

The set of standards can be used with an assay that changes in a concentration-dependent way to estimate the concentration of the molecule in the test sample, or to calibrate the settings of a device or machine that measures a characteristic of the molecule. A comparison is made of the signal from the unknown molecule to signals from known molecules using a variety of techniques known to those skilled in the art. By way of non-limiting example, proteins and nucleic acids are analyzed using techniques such as electrophoresis, sedimentation, chromatography, and mass spectrometry.

For example, one basic characteristic of a molecule is its molecular weight (MW). Comparison of an uncharacterized molecule to a set of standards of known and different molecular weights (often called a molecular weight "ladder") allows a determination of the apparent molecular weight of the uncharacterized molecule.

For example, proteins, nucleic acids and other molecules are electrophoresed or subjected to high pressure liquid chromatography (HPLC) in order to determine basic characteristics thereof. The MW of an uncharacterized protein can be estimated using HPLC, or electrophoresis, such as polyacrylamide electrophoresis (PAGE), including SDS-PAGE, and other techniques known in the art.

A variety of protein and nucleic acid molecular weight standards are commercially available. However, the molecular weight standards may not correspond closely enough in size to the unknown sample protein to allow an accurate estimation of apparent molecular weight. Moreover, some of the standards give poorly resolved (e.g., "fuzzy") bands. Some are not useful for hybridization techniques (Southerns, Northerns, Westerns, etc.) because they do not transfer well to nitrocellulose or PVDF membranes. Others comprise co-migrating contaminants. All of these effects operate to reduce the precision and accuracy of the analytical method.

Protein standards of higher MWs (e.g., greater than from about 180 to about 500 kD) are problematic. In addition to the potential problems that apply to MW standards in general, high MW proteins are hard to prepare, whether by recombinant DNA technology or otherwise. Many of these formed by cross-linking a single species of a protein to obtain a series of multimers of the protein that have molecular weights that are 2-fold, three-fold, etc., of the MW of the protein monomer (for example, Sigma sells cross-linked Hemoglobin, having an apparent molecular weight of 280 kDa). Cross-linkers are added by chemical reactions, and it is often difficult to establish reaction conditions wherein multimerization proceeds to the desired degree. Moreover, crosslinking is ordinarily performed using reagents that react with functional groups on a molecule. Generally there are more than one such reactive functional group on a protein, so when protein molecules are crosslinked, a variety of products results. For example, if a protein has as few as 4 reactive sites, 16 different crosslinked entities would be formed leading to inhomogeneity in the marker.

Moreover, the degree of homogeneity in a molecular population of a protein is also affected by, among other things, the different types and extents of post-translational and other chemical modifications thereof. The modifications range from amino acid changes through to the addition of macromolecules: lipid, carbohydrate or protein. Also chemical modifications such as phosphorylation, alkylation, deamidation and such can occur. Many variants of the common amino acids can occur, which can affect the structure or function of the protein. A major class of modification includes glycosylation, which may be N-linked, O-linked, or glycosylphosphatidylinositol (GPI)-linked. Such modifications have roles in protein stability and folding, targeting and recognition. Lipid modification of proteins (e.g., prenylation, myristoylation, GPI-anchoring, etc.) is also common. See Nalivaeva et al., Post-translational Modifications of Proteins: Acetylcholinesterase as a Model System, Proteomics 1:735-747 (2001).

For proteins, a non-exhaustive list of exemplary protein molecular weight standards (protein molecular weight "ladders") includes the following:

The pre-stained Broad Range protein molecular weight standard (Bio-Rad Laboratories, Hercules, Calif., Cat. No. 16001-018), which is composed of eight proteins:

| Protein | Molecular Weight (kDa) |
| --- | --- |
| Myosin (H-chain) | 209 |
| beta-Galactosidase | 124 |
| Bovine Serum Albumin | 80 |
| Ovalbumin | 49 |
| Carbonic Anhydrase | 34 |
| Soybean Trypsin Inhibitor | 29 |
| beta-Lactoglobulin | 21 |
| Aprotinin | 7.1 |

Protein Molecular Weight Markers, HPLC

| Protein | Molecular Weight (kDa) |
| --- | --- |
| Glutamate dehydrogenase | 290.00 |
| Lactate dehydrogenase | 142.00 |
| Enolase | 67.00 |
| Myokinase | 32.00 |
| Cytochrome c | 12.40 |

High Molecular Weight Protein Standards (Bio-Rad):

| Protein | Molecular Weight (kDa) |
| --- | --- |
| Myosin | 200.00 |
| beta-Galactosidase | 116.25 |
| Phosphorylase B | 97.40 |
| Serum Albumin | 66.20 |
| Ovalbumin | 45.00 |

Molecular weight markers, $^{14}$C-methylated For Molecular Weights 14,300-220,000 (Sigma M8932), which is a mixture of six $^{14}$C-methylated proteins:

| Protein | Molecular Weight (kDa) |
| --- | --- |
| Myosin | 220.00 |
| Phosphorylase b | 97.40 |
| Albumin, Bovine Serum | 66.00 |
| Ovalbumin | 46.00 |
| Carbonic Anhydrase | 30.00 |
| Lysozyme | 14.30 |

Molecular weight markers, $^{14}$C-methylated For Molecular Weights 2,350-30,000 (Sigma M8807), which is a mixture of five $^{14}$C-methylated proteins:

| Protein | Molecular Weight (kDa) |
| --- | --- |
| Carbonic Anhydrase | 30.00 |
| Soybean Trypsin Inhibitor | 21.50 |
| Cytochrome c | 12.50 |
| Aprotinin | 6.50 |
| Insulin (Bovine) | 5.74* |

*After sample preparation, the bovine insulin will probably migrate as insulin a chain (2.35 kDa) and insulin b chain (3.40 kDa)

PEPPERMINTSTICK™ phosphoprotein molecular weight standards (Molecular Probes, P-33350):

| Protein | Molecular Weight (kDa) |
| --- | --- |
| beta-Galactosidase | 116.25 |
| Albumin, Bovine Serum | 66.20 |
| Ovalbumin | 45.00 |
| Beta-Casein | 23.60 |
| Avidin | 18.00 |
| Lysozyme | 14.40 |

A need exists for homogeneous populations of molecules having a known value for a molecular characteristic. Such populations can be compared to an uncharacterized molecule in order to estimate or determine the presence or absence of, or value for, a molecular characteristic.

A need exists for sets of molecules (molecular standards) having a known value for a molecular characteristic, such as molecular weight, wherein the value for the molecular characteristic is precise. A particular need exists for protein standards (protein "ladders") that comprise proteins having a high molecular weight.

Patents and Published Patent Applications of Interest:
U.S. Pat. No. 5,449,758 (Protein Size Marker Ladder).
U.S. Pat. No. 5,580,788 (Use of Immunoglobulin-Binding Artificial Proteins as Molecular Weight Markers).
U.S. Pat. No. 5,714,326 (Method for the Multiplexed Preparation of Nucleic Acid Molecular Weight Markers and Resultant Products).
U.S. Pat. No. 5,578,180 (System for pH-neutral Longlife Precast Electrophoresis Gel).
U.S. Pat. No. 6,514,938 and published U.S. Patent Application US/2002/0115103 (Copolymer 1 Related Polypeptides for use as Molecular Weight Markers and for Therapeutic Use).
Published PCT patent application WO 02/13848 and published U.S. Patent Application US/2002/0155455 (Highly Homogeneous Molecular Markers for Electrophoresis).

SUMMARY OF THE INVENTION

The present invention provides a purified population of macromolecules that have been treated by the addition, removal or modification of chemical groups, so as to be made at least partly homogeneous, for one or more molecular characteristics. The macromolecules are typically molecular standards that can be nucleic acids or proteins. In certain aspects of the invention, the molecular standards are polypeptides, such as oligopeptides and that are part of a protein, or the molecular standards are nucleic acids, such as a DNA, RNA or oligonucleotides.

In certain aspects, the population of macromolecules is a population of protein standards.

In one embodiment, the present invention provides an isolated high molecular weight protein standard. The protein standard typically has an apparent molecular weight of at least 300 kDa by SDS PAGE, and can have an apparent molecular weight, for example, of 400 kDa, 450 kDa, 500 kDa, 600 kDa, 700 kDa, 750 kDa, or 1000 kDa.

In certain aspects, the isolated high molecular weight protein standard does not include at least one post-translational modification that is usually present on the protein in vivo. For example, the absence of a post-translational modification can be the result of chemical modification of the protein carried out according to a method provided herein.

In illustrative embodiments, the molecular weight standard is a chemically modified high molecular weight protein. The isolated high molecular weight protein standard in certain aspects does not include a phosphate group, a carbohydrate group, an amide, an N-terminal modification, an isoprenoid group, a selenium group, a sulfate group, a disulfide bond, a fatty acid group, a hydroxyl group, and/or a ubiquitin group.

In certain aspects, the protein standard is a laminin polypeptide. In certain examples, the laminin polypeptide does not include a carbohydrate group or a disulfide bond, and optionally includes an alkyl group.

In certain aspects, the isolated high molecular weight protein standard is at least partially homogeneous, or completely homogeneous.

In another embodiment, provided herein, is a method for preparing a protein standard, comprising modifying an isolated protein by removing, adding, or modifying a chemical modification of the isolated protein to produce a modified protein, thereby preparing the protein standard.

In certain illustrative examples, the chemical modification of the isolated protein is a post-translational modification. Furthermore, in certain illustrative examples, the modification of the isolated protein is carried out for a population of isolated proteins to produce an at least partially homogeneous population of the protein standard, or a completely homogeneous population of the protein standard, for one, many, or all molecular characteristics. Additionally, the method can be carried out for a series of isolated proteins having different molecular characteristics. For example, the method can be carried out for a series of isolated proteins having different molecular weights.

The method can be carried out, for example, for a population of each of a series of isolated proteins having different molecular characteristics resulting in a series of at least partially homogeneous populations of proteins, or a series of completely homogeneous populations of proteins. The series of isolated proteins, for example, can be a series of high molecular weight proteins, such as high molecular weight standards. The series can also include other molecular weight standards, that for example, are of a lower molecular weight.

In illustrative examples, the at least partially homogeneous population of proteins is a population of high molecular weight proteins. For example, the population of proteins can include a laminin polypeptide.

The removing, adding, or modifying in certain aspects of the invention includes adding, removing, or modifying from an isolated protein, a phosphate group, a carbohydrate group, an amide, an N-terminal modification, an isoprenoid group, a selenium group, a sulfate group, a fatty acid group, a hydroxyl group, or an ubiquitin group. In one example, a phosphate group is removed from the population of isolated proteins, to produce an at least partially homogeneous population of the protein standard, or a completely homogeneous population of the protein standard, especially with respect to the presence of the group being added, removed, or modified.

In certain aspects, a population of a laminin polypeptide is modified. For example, the modification can include deglycosylation, reduction, and/or alkylation. The invention also provides an isolated molecular weight standard produced according to the methods provided herein.

In another embodiment, provided herein is a kit comprising an isolated high molecular weight standard produced using the methods provided herein. The kit can further include a molecular weight protein standard that is not a high molecular weight protein standard.

In certain aspects, the kit further includes software for using the isolated high molecular weight standard to determine the molecular weight of an on-test protein. The uncharacterized and/or on-test molecule can be a polypeptide, an oligopeptide, or a protein, or can be a nucleic acid, such as DNA, RNA or an oligonucleotide.

In another embodiment, the present invention provides a set of molecular standards that comprises (a) one or more molecules having at least one known value for at least one molecular characteristic and (b) at least one homogeneous population of the one or more molecules. In various embodiments, homogeneous populations of molecules are prepared by adding, deleting or changing one or more chemical modifications to the molecules to produce a population of modified molecules. In some embodiments, the chemical modifications are post-translational modifications of proteins. The methods of preparing homogeneous populations of molecules can optionally comprise purifying or partially purifying modified molecules and/or eliminating or partially eliminating molecules that have not been modified as desired.

The present invention further provides a method of using a molecular standard to estimate or determine one or more characteristics of an uncharacterized and/or on-test molecule, wherein the molecular standard (a) comprises one or more molecules having at least one known value for at least one molecular characteristic and (b) comprises at least one homogeneous population of a molecule, wherein the method comprises subjecting the molecular standard and the uncharacterized molecule to a condition, and comparing the molecular standard to the uncharacterized and/or on-test molecule.

In certain aspects of the invention, the condition to which the molecular standard and the uncharacterized molecule are subjected to involves separating (resolving) the molecules and detecting the resolved molecules. Methods of separation include for example, electrophoresis and chromatography. Methods of separation can be based upon molecular weight, molecular size (e.g., Stoke's radius), charge, isoelectric point (pI) or any other molecular characteristic that can be detected, preferably quantified.

In certain methods provided herein, the modified protein is used as a standard in an analytical method. For example, the present invention provides molecular standards that can be used to calibrate an instrument with regard to one or more molecular characteristics. In some embodiments, the molecular characteristic is molecular weight (MW), which may be an apparent MW or an actual MW.

In certain aspects of the invention, the molecules in the molecular standard are pre-stained. Furthermore, in illustrative aspects of the invention, the a molecular standard provided herein is used as a molecular weight standard in gel electrophoresis, such as a protein standard for protein gel electrophoresis. The present invention also provides kits that include the high molecular weight protein standards of the present invention, or kits for carrying out the methods provided herein.

Other features and advantages of the invention will be apparent from the following detailed description and claims.

BRIEF DESCRIPTION OF THE DRAWINGS

FIGS. 4A and 4B show results of electrophoretic experiments. FIG. 4A is an image of a 3-8% Tris-Acetate gel that has been electrophoresed and stained; lane 1, laminin deglycosylated with PNGase F; lane 2, untreated laminin. FIG. 4B is an image showing a molecular weight standard comprising the laminin subunits (the upper three bands) that have been deglycosylated and reduced and alkylated.

DETAILED DESCRIPTION

Figure 1A:
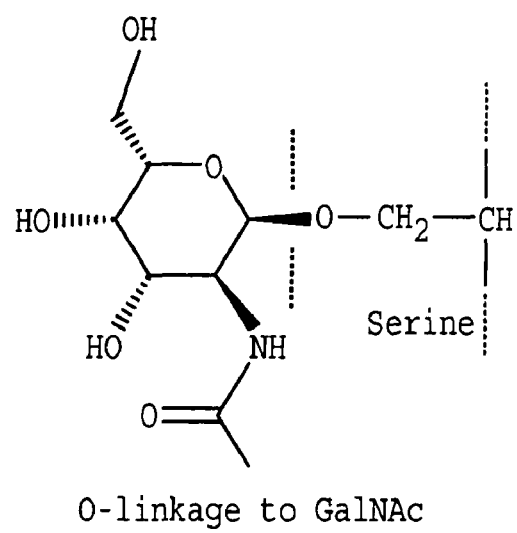
FIG. 1A shows the structure of an O-linkage to GalNAc.

Please note: The headings used herein are for convenience only.

---

CONTENTS

GENERAL DISCUSSION OF THE INVENTION
I. PROTEIN MODIFICATIONS
   A. Glycosylation
   B. Cross-Linking Modifications
   C. C-terminal Modifications
   D. N-terminal Modifications
   E. Phosphorylation
   F. Methylation/Prenylation
   G. Selenoproteins
   H. Sulfation
   I. Fatty Acid Modifications
   J. Other Types of Protein Modifications
II. CHANGING THE TYPE AND/OR AMOUNT OF PROTEIN MODIFICATION
   A. In Vivo Methods of Modifying Proteins
   B. In Vitro Methods of Modifying Proteins
      1. Chemically Modifying Proteins
      2. Enzymatically Modifying Proteins
III. DETECTION AND ANALYSIS OF MODIFIED PROTEINS
   A. In General
   B. Amidation
   C. Glycosylation and Deglycosylation
   D. Phosphorylation
IV. APPLICATIONS
   A. Electrophoresis
   B. Capillary Electrophoresis (CE)
   C. High Throughput Screening (HTS)
   D. Kits
   E. Pre-Stained High Molecular Weight Markers

---

The present invention is based in part on the discovery that an improved molecular standard can be produced by modifying a population of a species of isolated molecular standards, to further modify, add, or remove chemical groups on the molecular standards, to make the isolated molecular standards at least partially homogeneous for one or more molecular characteristics.

The present invention provides a purified population of macromolecules that have been treated by the addition, removal or modification of chemical groups, so as to be made at least partly homogeneous, for one or more molecular characteristics. The macromolecules are typically molecular standards that can be nucleic acids or proteins. In certain aspects of the invention, the molecular standards are polypeptides, such as oligopeptides and that are part of a protein, or the molecular standards are nucleic acids, such as a DNA, RNA or oligonucleotides.

In certain aspects, the population of macromolecules is a population of protein standards.

In one embodiment, the present invention provides an isolated high molecular weight protein standard. The protein standard typically has an apparent molecular weight of at least 250 kDa by SDS PAGE, and can have an apparent molecular weight, for example, of 300 kDa, 350 kDa, 400 kDa, 450 kDa, 500 kDa, 600 kDa, 700 kDa, 750 kDa, or 1000 kDa.

In certain aspects, the isolated high molecular weight protein standard does not include at least one post-translational modification that is usually present on the protein in vivo. For example, the absence of a post-translational modification can be the result of chemical modification of the protein carried out according to a method provided herein. Inc certain aspects, the protein standard is pre-stained (i.e. dye conjugated or dye-labeled before being analyzed by a protein separation technique).

In illustrative embodiments, the molecular weight standard is a chemically modified high molecular weight protein. The isolated high molecular weight protein standard in certain aspects does not include a phosphate group, a carbohydrate group, an amide, an N-terminal modification, an isoprenoid group, a selenium group, a sulfate group, a disulfide bond, a fatty acid group, a hydroxyl group, and/or a ubiquitin group.

In certain aspects, the protein standard is a laminin polypeptide. In certain examples, the laminin polypeptide does not include a carbohydrate group or a disulfide bond, and optionally includes an alkyl group. In other examples, the high molecular weight protein standard is apolipoprotein B or human kinase (Sigma, St. Louis, Mo.).

In certain aspects, the isolated high molecular weight protein standard is at least partially homogeneous, or completely homogeneous.

In certain aspects, the isolated high molecular weight protein standard is at least partially homogeneous, or completely homogeneous.

A "molecular characteristic" is any property of a molecule or population of molecules that can be detected and/or measured. The most fundamental "molecular characteristic" of a molecular species is its presence or absence in a composition. The invention provides compositions and methods to detect the absence or presence of a homogeneous population of macromolecules. By way of non-limiting example, a homogeneous population of macromolecules may be used to confirm that macromolecules and other molecules are electrophoresing, flowing or otherwise moving through an analytical or preparative media. Because of its homogeneous state, such a population of macromolecules provides a sharp signal as it is detected as it moves into, through or out of the media. A homogeneous population of macromolecules can be used in such embodiments even if it is the only molecular species and/or no molecular characteristic other than the presence or absence thereof is known.

A molecular characteristic may, but need not, be one that can be used to distinguish one molecular species from another. The molecular characteristic may, but need not, be one that can be detected and/or measured in other molecular species. The molecular characteristic may, but need not, be one that can be measured (either qualitatively or quantitatively) for both a known (previously characterized) macromolecule and an uncharacterized molecule. In the latter instance, the presence, absence, or amount of the signal from a known macromolecule can be compared with that of an uncharacterized molecule, in order to determine the presence or absence of the uncharacterized molecule, and/or to estimate or determine a value for the molecular characteristic of the uncharacterized molecule.

By "homogenous or partly so," "homogeneous or partly so," "at least partly homogeneous," or "at least partly homogenous," it is meant that the population of macromolecules is homogeneous, nearly homogeneous, homogeneous to a detectable limit, and/or homogeneous to the extent needed to be used to practice the invention. In certain aspects, the population of macromolecules, such as a population of protein standards is at least 50%, 60%, 70%, 75%, 80%, 90%, 95%, 99%, or 100% (i.e. completely) homogeneous. By "homogeneous" or "homogenous" is meant that the population of macromolecules is identical with respect to their molecular structure. In other words, if a protein is ordinarily glycosylated, a population of the protein likely includes individual protein molecules that include different numbers of carbohydrate groups and/or different types of carbohydrates. However, if the glycosylated protein is made homogeneous using the methods disclosed herein, the population is completely or 100% homogeneous with respect to glycosylation when all of the molecules of the protein in the population have identical carbohydrate moieties attached at identical residues, or lack a carbohydrate moiety altogether. Therefore, the population can be homogeneous with respect to a particular characteristic (e.g., glycosylation), or can be homogeneous with respect to all characteristics.

The macromolecules may be polymers, including polymers from natural sources, such as proteins and nucleic acids. In some embodiments wherein the macromolecule is a protein, the modification may be related to a post-translational modification such as the presence, absence, or quantity of phosphate groups, carbohydrate groups, amides, N-terminal modifications, isoprenoid groups, selenium groups, sulfate groups, disulfide bonds, fatty acid groups, hydroxyl groups, and/or ubiquitin groups.

The present invention further provides molecular standards that may be used to estimate or determine one or more characteristics of an uncharacterized molecule, wherein the molecular standard comprises two or more molecules, at least one of which is homogeneous. In some embodiments, the molecular characteristic is molecular weight (MW), which may an apparent MW or an actual MW. In one embodiment, the present invention provides one or more high molecular weight standards. For example, the invention provides a set of molecular weight standards wherein at least one standard is greater 250, 300, 350, 400, 450, 500, 550, 600, 650, 700, 750, or 1000 kDa. An exemplary set of molecular weight standards is the HIMARK™ standard set illustrated in the Examples herein.

By "high molecular weight" protein standard it is meant that the actual or apparent MW is greater than or equal to about 200 kDa to about 10,000 kDa, e.g., ≧about 250 kDa, ≧about 300 kDa, ≧about 350 kDa, ≧about 400 kDa, ≧about 450 kDa, ≧about 500 kDa, ≧about 550 kDa, ≧about 600 kDa, ≧about 650 kDa, ≧about 700 kDa, ≧about 750 kDa, ≧about 800 kDa, ≧about 850 kDa, ≧about 900 kDa, ≧about 950 kDa, ≧about 1,000 kDa, ≧about 2,000 kDa, ≧about 5,000 kDa, ≧about 7,500 kDa, and ≧about 10,000 kDa, etc.

In another embodiment, provided herein, is a method for preparing a protein standard, comprising modifying an isolated protein by removing, adding, or modifying a chemical modification of the isolated protein to produce a modified protein, thereby preparing the protein standard.

In certain illustrative examples, the chemical modification of the isolated protein is a post-translational modification. Furthermore, in certain illustrative examples, the modification of the isolated protein is carried out for a population of isolated proteins to produce an at least partially homogeneous population of the protein standard, or a completely homogeneous population of the protein standard, for one, many, or all molecular characteristics. Additionally, the method can be carried out for a series of isolated proteins having different molecular characteristics. For example, the method can be carried out for a series of isolated proteins having different molecular weights.

The at least partially homogeneous population of molecules provided herein, is typically substantially pure. "Substantially pure" refers to a population of molecules that is substantially free of other biological molecules such as nucleic acids, proteins, lipids, carbohydrates or other materials with which it is naturally associated. Substantially purified or "isolated" refers to molecules, either nucleic or amino acid sequences, that are removed from their natural environment, isolated or separated, and are at least 60% free, preferably 75% free, and most preferably 90% free from other components with which they are naturally associated. One skilled in the art can isolate molecules using standard techniques for biomolecular purification. A substantially pure or pure polypeptide will yield a single major band on a non-reducing polyacrylamide gel. An "isolated" or "purified" molecule is at least 90% free from other components with which it is naturally associated.

The method of the invention can be carried out, for example, for a population of each of a series of isolated proteins having different molecular characteristics resulting in a series of at least partially homogeneous populations of proteins, or a series of completely homogeneous populations of proteins. The series of isolated proteins, for example, can be a series of high molecular weight proteins, such as high molecular weight standards. The series can also include other molecular weight standards that for example, are of molecular weights that are lower than the high molecular weight standards.

In illustrative examples, the at least partially homogeneous population of proteins is a population of high molecular weight proteins that can be standards. For example, the population of proteins can include one or more laminin polypeptides. For example, the laminin polypeptide can be a laminin alpha chain, a laminin beta chain, and/or a laminin gamma chain. In certain aspects, the invention provides a molecular weight standard set that includes an at least partially homogeneous population of laminin alpha chain, laminin beta chain, and laminin gamma chain. The molecular weight standard set is useful, for example, for determining the molecular weight for an on-test and/or unknown protein run on the same gel as the protein standard. The laminin alpha protein can have an estimated molecular weight, for example, of 425-525 kDa, 475-525, or in one example 500 kDa. The laminin beta protein can have an estimated molecular weight, for example, of 200-375 kDa, 250-325 kDa, or in illustrative example, 290 kDa. The laminin gamma protein can have an estimated molecular weight, for example, of 200-300 kDa, 225-275 kDa, or in certain aspects, 240 kDa.

The removing, adding, or modifying in certain aspects of the invention includes adding, removing, or modifying from an isolated protein, a phosphate group, a carbohydrate group, an amide, an N-terminal modification, an isoprenoid group, a selenium group, a sulfate group, a fatty acid group, a hydroxyl group, or an ubiquitin group. In one example, a phosphate group is removed from the population of isolated proteins, to produce an at least partially homogeneous population of the protein standard, or a completely homogeneous population of the protein standard, especially with respect to the presence of the group being added, removed, or modified.

In certain aspects, a population of a laminin polypeptide is modified. For example, as illustrated in the Examples provided herein, the modification can include deglycosylation, reduction, and/or alkylation. The invention also provides an isolated molecular weight standard produced according to the methods provided herein.

In another embodiment, provided herein is a kit comprising an isolated high molecular weight standard produced using the methods provided herein. The kit can further include a molecular weight protein standard that is not a high molecular weight protein standard.

In certain aspects, the kit further includes software for using the isolated high molecular weight standard to determine the molecular weight of an on-test protein. The uncharacterized and/or on-test molecule can be a polypeptide, an oligopeptide, or a protein, or can be a nucleic acid, such as DNA, RNA or an oligonucleotide. The kit in other aspects, include at least one of the at least partially homogeneous laminin proteins discussed herein.

In another embodiment, the present invention provides a set of molecular standards that comprises (a) one or more molecules having at least one known value for at least one molecular characteristic and (b) at least one homogeneous population of the one or more molecules. In various embodiments, homogeneous populations of molecules are prepared by adding, deleting or changing one or more chemical modifications to the molecules to produce a population of modified molecules. In some embodiments, the chemical modifications are post-translational modifications of proteins. The methods of preparing homogeneous populations of molecules can optionally comprise purifying or partially purifying modified molecules and/or eliminating or partially eliminating molecules that have not been modified as desired.

The present invention further provides a method of using a molecular standard to estimate or determine one or more characteristics of an uncharacterized and/or on-test molecule, wherein the molecular standard (a) comprises one or more molecules having at least one known value for at least one molecular characteristic and (b) comprises at least one homogeneous population of a molecule, wherein the method comprises subjecting the molecular standard and the uncharacterized molecule to a condition, and comparing the molecular standard to the uncharacterized and/or on-test molecule.

In certain aspects of the invention, the condition to which the molecular standard and the uncharacterized molecule are subjected to involves separating (resolving) the molecules and detecting the resolved molecules. Methods of separation include electrophoresis and chromatography. Methods of separation can be based upon molecular weight, molecular size (e.g., Stoke's radius), charge, isoelectric point (pI) or any other molecular characteristic that can be detected, preferably quantified.

In certain methods provided herein, the modified protein is used as a standard in an analytical method. For example, the present invention provides molecular standards that can be used to calibrate an instrument with regard to one or more molecular characteristics. In some embodiments, the molecular characteristic is molecular weight (MW), which may be an apparent MW or an actual MW.

In certain aspects of the invention, the molecules in the molecular standard are pre-stained. Furthermore, in illustrative aspects of the invention, the molecular standard provided herein is used as a molecular weight standard in gel electrophoresis, such as a protein standard for protein gel electrophoresis.

Other features and advantages of the invention will be apparent from the following detailed description and claims.

I. Protein Modifications

The following sections provide details regarding various protein modifications, which are examples of chemical modifications with respect to the present invention. These modifications can be affected in the methods provided herein in order to provide a more homogeneous protein population.

I.A. Glycosylation

Glycosylation at an -Asn-Xaa-Cys- site has been reported for coagulation protein C. N-linked sites are often indirectly assigned by the appearance of a "blank" cycle during sequencing. The oligosaccharide can be released by treatment with Peptide N Glycosidase F (PNGase F, available from Prozyme, San Leandro, Calif.), which converts the glycosylated Asn to Asp.

Glycoproteins consist of proteins covalently linked to carbohydrate. The predominant sugars found in glycoproteins are glucose, galactose, mannose, fucose, N-Acetyl-D-galactosamine (GalNAc), N-Acetyl-D-glucosamine (GlcNAc), and NANA (N-acetylneuraminic acid).

Figure 1B:
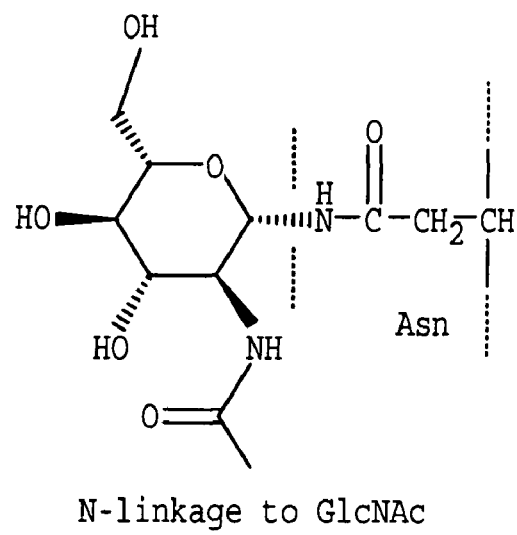
FIG. 1B shows the structure of an N-linkage to GalNAc.

The carbohydrate modifications found in glycoproteins include, by way of non-limiting example, carbohydrates that are linked to the protein component through either O-glycosidic or N-glycosidic bonds. The N-glycosidic linkage is through the amide group of asparagine. The O-glycosidic linkage is to the hydroxyl of serine, threonine or hydroxylysine. The linkage of carbohydrate to hydroxylysine is generally found only in the collagens. The linkage of carbohydrate to 5-hydroxylysine is either the single sugar galactose or the disaccharide glucosylgalactose. In Ser- and Thr-type O-linked glycoproteins, the carbohydrate directly attached to the protein is GalNAc. In N-linked glycoproteins, it is GlcNAc. FIG. 1A illustrates the structure of an O-linkage to GalNAc, and FIG. 1B illustrates the structure of an N-linkage to GlcNAc.

Figure 2A:
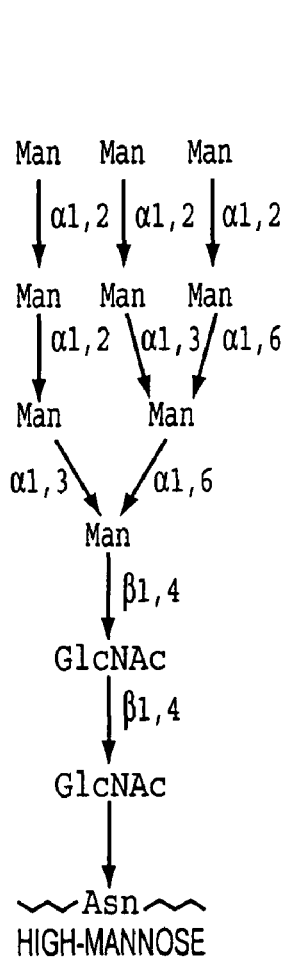
FIG. 2A shows the structure of a high-mannose family of N-linked sugar family.
Figure 2B:
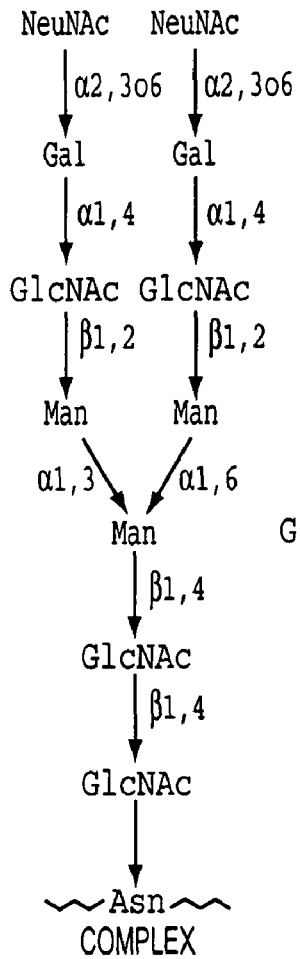
FIG. 2B shows the structure of a complex family of N-linked sugar family.
Figure 2C:
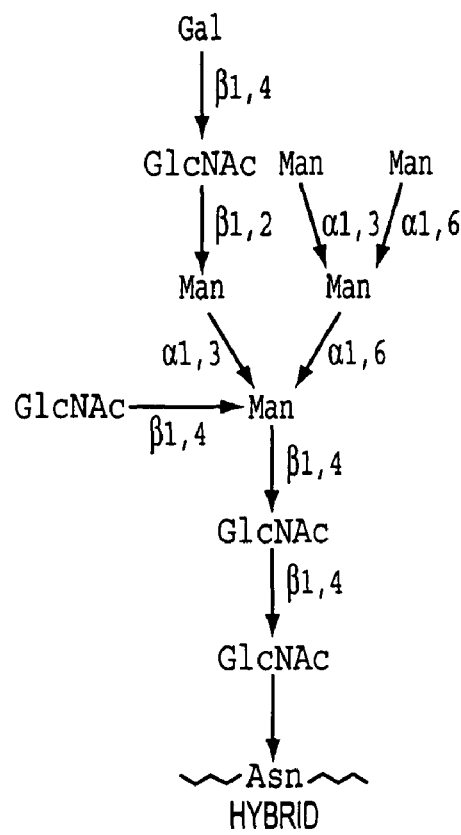
FIG. 2C shows the structure of a hybrid family of N-linked sugar family.

The predominant carbohydrate attachment in glycoproteins of mammalian cells is via N-glycosidic linkage. The site of carbohydrate attachment to N-linked glycoproteins is found within a consensus sequence of amino acids, N—X—S(T), where X is any amino acid except P (proline). N-linked glycoproteins all contain a common core of carbohydrate attached to the polypeptide. This core consists of three mannose residues and two GlcNAc. A variety of other sugars are attached to this core and comprise three major N-linked families (1) the high-mannose type (FIG. 2A), which contains all mannose outside the core in varying amounts; (2) the hybrid type (FIG. 2C), which contains various sugars and amino sugars; and (3) the complex type (FIG. 2B), which is similar to the hybrid type, but in addition, contains sialic acids to varying degrees.

I.B. Cross-Linking Modifications

Cystine ($-CH_2-S-S-CH_2-$) disulfides spontaneously form under oxidizing conditions; lanthionine ($-CH_2-S-CH_2-$) has also been found, often as an artifact of peptide synthesis. Intramolecular thioester linkages between Cys and Glu residues have been found in complement C3 and C4, and in alpha-2-macroglobulin. Epsilon-(gamma-glutamyl)lysine cross-links are catalyzed by transglutaminases such as factor XIIIa. Ubiquitin C-terminal COOH are similarly linked to Lys epsilon-amino groups.

I.C. C-Terminal Modifications

C-Terminal amidation is common in peptide hormones. The amide is contributed by Gly from a precursor C-terminal sequence of -XGXX.

I.D. N-Terminal Modifications

N-acetyl "blocked" N-termini of eukaryotic proteins are common; the N-terminal residues are often Ala, Ser, Met, Gly or Thr. N-acetyl residues can be enzymatically removed from peptides (Krishna, R. G (1992) in: Techniques in Protein Chemistry 111, pp. 77-84, Academic Press (San Diego). N-methylation of mammalian ribosomal proteins usually occurs at Ala/Pro/Phe-Pro-Lys-N-termini. N-formyl Met is usually processed by a deformylase. Glutamine and S-carboxy-methylcysteine can form cyclic "blocked" N-terminal residues; the former can be removed by pyroglutamate aminopeptidase.

Some proteins have the 14 carbon myristoyl group added to their N-termini. The donor for this modification is myristoyl-CoA.

I.E. Phosphorylation

Post-translational phosphorylation is one of the most common protein modifications that occurs in animal cells. It is estimated that ⅓ of all proteins present in a mammalian cell are phosphorylated and that kinases, enzymes responsible for phosphorylation, constitute about 1-3% of the expressed genome. The vast majority of phosphorylations occur as a mechanism to regulate the biological activity of a protein and as such are transient. In other words a phosphate (or more than one in many cases) is added and later removed.

The enzymes that phosphorylate proteins are termed kinases and those that remove phosphates are termed phosphatases.

That is, protein kinases catalyze the reaction:

ATP+Protein→Phosphoprotein+ADP

Whereas, in contrast, protein phosphatases catalyze the reaction:

Phosphoprotein+H2O→Protein+P_i

In animal cells serine, threonine and tyrosine are the amino acids subject to phosphorylation. The largest group of kinases are those that phosphorylate either serines or threonines and as such are termed serine/threonine kinases. The ratio of phosphorylation of three different amino acids is approximately 1000/100/1 for serine/threonine/tyrosine. However, a phosphate group can modify histidine, arginine, lysine, cysteine, glutamic acid and aspartic acid residues. However, the phosphorylation of hydroxyl groups at serine (90%), threonine (10%), or tyrosine (0.05%) residues are the most prevalent.

I.F. Methylation/Prenylation

Prenylation refers to the addition of the 15 carbon farnesyl group or the 20 carbon geranylgeranyl group to acceptor proteins, both of which are isoprenoid compounds derived from the cholesterol biosynthetic pathway. The isoprenoid groups are attached to cysteine residues at the carboxy terminus of proteins in a thioether linkage (C—S—C). A common consensus sequence at the C-terminus of prenylated proteins has been identified and is composed of CAAX, where C is cysteine, A is any aliphatic amino acid (except alanine) and X is the C-terminal amino acid. In order for the prenylation reaction to occur the three C-terminal amino acids (AAX) are first removed and the cysteine activated by methylation in a reaction utilizing S-adenosylmethionine as the methyl donor. For reviews, see Rando, "Chemical biology of protein isoprenylation/methylation", Biochim Biophys Acta 1300:5-16. (1996); and Toledo et al., "Methylation of proteins from the translational apparatus: an overview", Arch Biol Med Exp (Santiago) 21:219-229 (1988).

I.G. Selenoproteins

Selenium is a trace element and is found as a component of several prokaryotic and eukaryotic enzymes that are involved in redox reactions. The selenium in these selenoproteins is incorporated as a unique amino acid, selenocysteine, during translation. A particularly important eukaryotic selenoenzyme is glutathione peroxidase; this enzyme is required during the oxidation of glutathione by hydrogen peroxide ($H_2O_2$) and organic hydroperoxides. A selenocysteine residue in a protein has the general structure:

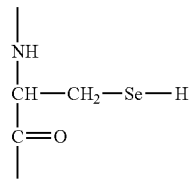

I.H. Sulfation

Sulfate modification of proteins occurs at tyrosine residues such as in fibrinogen and in some secreted proteins (e.g., gastrin). Generally, sulfate is added permanently.

Figure 3:
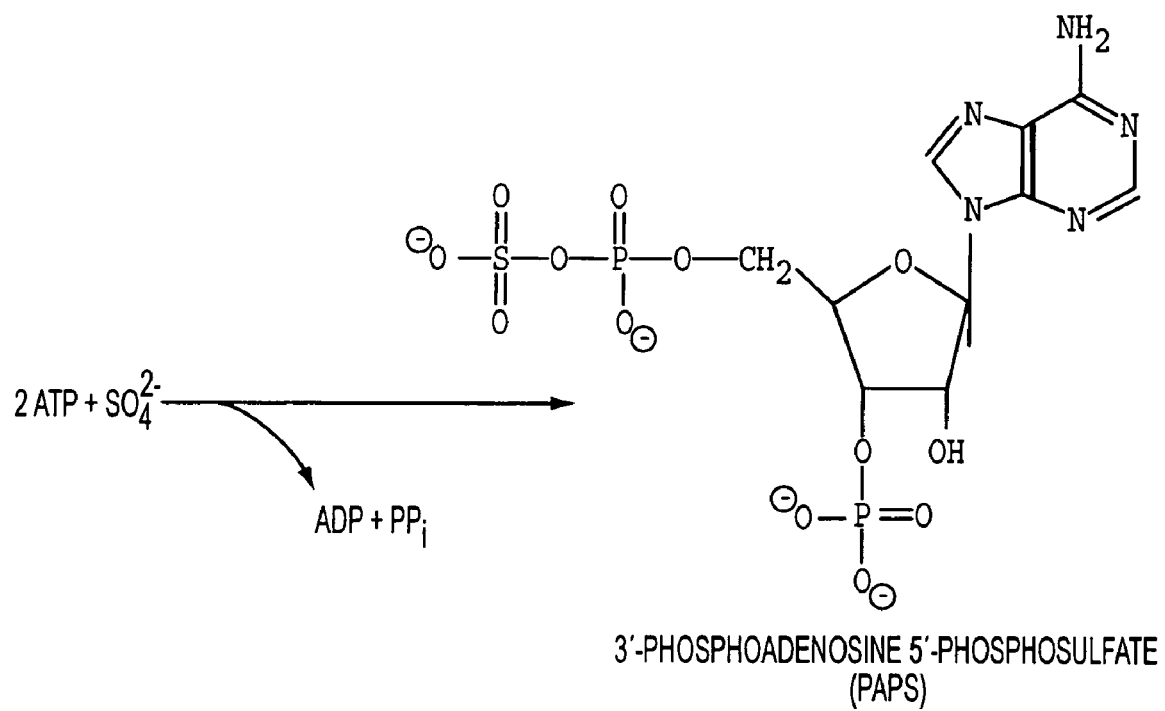
FIG. 3 shows the formation of 3'phosphoadenosine 5'-phosphosulfate.

The universal sulfate donor is 3'-phosphoadenosyl-5'-phosphosulphate (PAPS). The formation of PAPS is illustrated at FIG. 3.

I.I. Fatty Acid Modifications

Glycosylphosphatidylinositol (GPI) structures are found at the C-terminus of several membrane proteins (Ferguson, Biochem. Soc. Trans. 20:243-256, 1992). Ethanolamine phosphoglycerol attached to Glu residues generate "blank" sequencer cycles. Some membrane-spanning proteins have cytoplasmic Cys (or possibly Ser) residues that are acylated by palmitate or stearate. N-myristoylation can occur on proteins with N-terminal Gly residues (Sefton et al., J. Cell Biol 104:1449-1453, 1987; Grand, Biochem. J. 258:625-638, 1989) or on the epsilon-amino side chain of Lys (Stevenson et al., Proc. Natl. Acad. Sci. 90, 7245-7249, 1993). Acyl groups can be identified by GC, GC-MS analysis or by RP-HPLC after acid hydrolysis, extraction with ether or chloroform, and methylation. S- or O-acyl groups will be removed by base (0.1 M methanolic KOH, 90 min, 23° C.) or hydroxylamine (1 M $NH_2OH$, 20 hr, pH 7, 23° C.) treatment, while N-acyl groups are base- and hydroxylamine-stable and cause "blocked" N-termini. Lipoic acid groups have also been found on Lys. Isoprenylation of Cys residues has been reported for Ras-type proteins (Clarke, Annu. Rev. Biochem. 61:355-386, 1992). Geranylgeranyl (C20) or farnesyl (C15) isoprenoids are added to Cys side chains at -Cys-Aaa-Aaa-Xaa C-termini, then the Aaa-Aaa-Xaa tripeptide is removed, followed by methylation of the COOH.

I.J. Other Protein Modifications

Other non-limiting example of post-translational modifications include hydroxylation, ADP-ribosylation, carboxylation, adenylation and ubiquitination. For a review, see Han et al., "Post-translational chemical modification(s) of proteins", Int J Biochem 24:19-28 (1992). Post-translational bromination of tryptophan residues is also known (Jimenez et al., "Bromocontryphan: post-translational bromination of tryptophan", Biochemistry 36:989-994 (1997).

II. Changing the Type and/or Amount of Protein Modification

The following section provides of exemplary methods that can be used to remove, add, or modify, a chemical modification present on a protein.

II.A. In Vivo Methods of Modifying Proteins

A method for making amidated peptides using a modified self-cleaving vacuolar membrane ATPase (VMA) intein expression system is described by Cottingham et al., "A method for the amidation of recombinant peptides expressed as intein fusion proteins in *Escherichia coli*", Nat Biotechnol 19:974-977 (2001).

Recombinant expression of proteins in *Escherichia coli* may result in glycosylation. See Mironova et al., "Evidence for non-enzymatic glycosylation in *Escherichia coli*", Mol Microbiol 39:1061-1068 (2001).

Genetic engineering techniques have been used to replace cysteine residues in proteins with selenocysteine. See, for example, Koishi et al., "Production of Functional Human Selenocysteine-Containing KDRF/Thioredoxin Reductase in *E. coli*", J. Biochem. 127:977-983 (2000); and Stadtman, "Selenocysteine" (review), Annu Rev Biochem. 65:83-100 (1996).

Protein production and maturation in *Saccharomyces cerevisiae* is described by Schuster et al., "Protein expression in yeast; comparison of two expression strategies regarding protein maturation", J Biotechnol 84:237-248 (2000).

The post-translational machinery of *Pichia pastoris* has allowed for the production of functional mammalian glycoproteins. See Crosier et al., "New insights into the control of cell growth; the role of the AxI family" Pathology 29:131-135 (1997).

Methods of modulating and/or modifying post-translational processing, including N-glycosylation, in insect cells are known. See Ailor et al., "Modifying secretion and post-translational processing in insect cells", Curr Opin Biotechnol 10:142-145 (1999); and Jarvis et al., "Engineering N-glycosylation pathways in the baculovirus-insect cell system" (review), Curr Opin Biotechnol 9:528-533 (1998).

II.B. In Vitro Methods of Modifying Proteins

II.B.1. Chemically Modifying Proteins

II.B.1a. Chemical Amidation

The following are representative teachings regarding chemical amidation that can be used to practice the invention: Bradbury et al., Peptide Amidation, Trends Biochem Sci 16:112-115 (1991); and Eipper et al., Peptide Alpha-Amidation, Annu Rev Physiol 50:333-344 (1988).

II.B.1b. Chemical Glycosylation and Deglycosylation

The following are representative teachings or compositions regarding chemical deglycosylation that can be used to practice the invention: GLYCOFREE™ Chemical Deglycosylation Kit (Prozyme, San Leandro, Calif., USA).

II.B.2. Enzymatically Modifying Proteins

II.B.2.a. Enzymatic Amidation

The following are representative teachings regarding enzymatic amidation that can be used to practice the invention: Wu et al., "In Vitro Amidating Processing of Products Expressed by Gene Engineering", Acta Biochemica et Biophysica Sinica (Shanghai) 32:312-315 (2000), which describes recombinant rat peptidylglycine alpha-amidating monooxygenase (rPAM); Merkler, "C-terminal Amidated Peptides: Production by the In Vitro Enzymatic Amidation of Glycine-Extended Peptides etc.", Enzyme Microb Technol 16:450-456 (1994); and Breddam et al., "Amidation of Growth Hormone Releasing Factor (1-29) by Serine Carboxypeptidase Catalysed Transpeptidation", Int J Pept Protein Res 37:153-160 (1991).

II.B.2.b. Deamination—Amidohydrolases

According to the categorical numbering system of EC (Schomburg, D. & Salzmann, M., eds. (1991) Enzyme Handbook 4 (Springer, Berlin) that uses such properties as substrate specificity and physicochemical characteristics as criteria, amidohydrolases have been divided into two major types: 77 were included in the EC 3.5.1 category (EC 3.5.1.1-3.5.1.77), and 14 were placed under EC 3.5.2 (EC 3.5.2.1-3.5.2.14).

Amidohydrolases that can be used to practice the invention include recombinantly produced amidohydrolases, which may be enantioselective. See, e.g., Fournand et al., "Acyl transfer activity of an amidase from *Rhodococcus* sp. strain R312: formation of a wide range of hydroxamic acids", Applied and Environmental Microbiology 64:2844-2852 (1998).

II.B.2.c. Glycosylation and Deglycosylation

Enzymes catalyzing the addition (O-GlcNAc transferase, OGT) and removal (O-GlcNAcase) of the N-glycosylation have been cloned and expressed using recombinant DNA technology. These and other enzymes of the disclosure can likewise be cloned for expression in bacterial hosts (Vosseller et al., "Nucleocytoplasmic O-glycosylation: O-GlcNAc and functional proteomics", Biochimie 83:575-581, 2001).

The following are representative of glycosylases and deglycosylases that can be used to practice the invention:

Enzymes available from New England Biolabs (Beverly, Mass.) include:

N-Glycosidase F (PNGase F) from *Flavobacterium meningosepticum*
Endoglycosidase H (Endo H)
Endo Hf (a protein fusion of Endo H and maltose binding protein)

Enzymes available from Prozyme (San Leandro, Calif.):

Enzymatic Deglycosylation Kit
GLYKO ® Enzymatic Deglycosylation Kit
GLYKO ® Deglycosylation Plus
Ceramide-Glycanase from *Marobdella decora*
Sialidase from *S. pneumoniae* recombinant in *E. coli*
Sialidase from *C. perfingens* recombinant in *E. coli*
Sialidase from *A. ureafaciens* recombinant in *E. coli*
Beta-N-acetylhexosaminidase from *S. pneumoniae* recombinant in *E. coli*
Alpha-Mannosidase from *X. manihotis* recombinant in *E. coli.*
O-Glycanase from *S. pneumoniae* recombinant in *E. coli*
Endoglycosidase-H from *S. plicatus* recombinant in *E. coli*
Beta-Galactosidase from *X. manihotis* recombinant in *E. coli.*
Beta-Xylosidase from *A. niger*
Alpha-Fucosidase from *X. manihotis* recombinant in *E. coli.*
Alpha-Fucosidase from *A. niger* recombinant in *E. coli.*
Chondroitinase ABC from *P. vulgaris* recombinant in *A. niger*
Endo-beta-galactosidase from *Bacteroides fragiles*
Endoglycosidase H (recombinant)
PNGase F (*Chryseobacterium* [*Flavobacterium*] *meningosepticum*)
Endo-alpha-N-acetylgalactosaminidase
Endoglycosidase-F1 from *Flavobacterium meningosepticum*
N-Glycanase (recombinant)
Endoglycosidase-F1 from *Flavobacterium meningosepticum*
Endoglycosidase-F2 from *Flavobacterium meningosepticum*
Endoglycosidase-F3 from *Flavobacterium meningosepticum*
N-GLYCANASE ™-PLUS PNGase F (recombinant)
Heparinase I (*Flavobacterium heparinum*)
Chondroitinase ABC
Chondroitinase ACI Rev 29/12/96

-continued alpha-L-Iduronidase (Human liver - recombinant)
beta(1-3,4,6)-D-Glucuronidase (Bovine liver)
alpha-N-Acetylglucosaminidase (Human urine - recombinant)
Iduronate-2-sulfatase (Human liver - recombinant)
Glucosamine-6-sulfatase (Caprine liver - recombinant)
Sulfamidase (Human liver - recombinant)
Galactosyltransferase
Fucosyltransferase
alpha-N-Acetylgalactosaminidase (Chicken liver)
beta(1-2,3,4,6)-N-Acetylhexosaminidase (Jack bean)
Beta-N-Acetylhexosaminidase
alpha(1-2,3,4,6)-Fucosidase (Bovine kidney)
alpha(1-3,4,6)-Galactosidase (Green coffee bean)
alpha-Mannosidase (*Aspergillus saitoi*)
alpha(1-2,3,6)-Mannosidase (Jack bean)
Sialidase (*Arthrobacter ureafaciens*)
beta(1-3,4,6)-Galactosidase (Jack bean)
beta(1-3,4)-Galactosidase (Bovine Testes)
beta (1-4)-Galactosidase (*Streptococcus pneumoniae*)
beta-Mannosidase (*Helix pomatia*)
Sialidase [Neuraminidase] (*Clostridium perfingens*)
SIALIDASE N ™ (Newcastle disease virus, Hitchner B1 Strain)
SIALIDASE N ™ (recombinant)
alpha(1-3,4)-Fucosidase (Almond meal)
SIALIDASE V ™ (*Vibrio cholerae*)
Sialidase I (recombinant)
Sialidase (*Arthobacter ureafaciens*)

II.B.2.d. Phosphatases

The following are representative of phosphatases that can be used to practice the invention:

Members of the serine/threonine protein phosphatase family, including the prototype-member, protein phosphatase-1 (phosphorylase phosphatase; originally named PR enzyme). For a review, see Lee et al., Phosphorylase Phosphatase: New Horizons for an Old Enzyme, Frontiers in Bioscience 4:d270-285 (1999).

Alkaline phosphatases, such as calf intestine alkaline phosphatase (Stratagene, Promega) and alkaline phosphatase from *E. coli* (CHIMERx, Milwaukee, Wis.).

II.B.1b(2)(v) Kinases

The following are representative of kinases that can be used to practice the invention: members of the eukaryotic protein kinase (EPK) family, including human members (Kostichl et al., Human Members of the Eukaryotic Protein Kinase Family, Genome Biology 3: research0043.1-0043.12 (2002); members of the calmodulin-protein kinase family; and members of the mitogen-activated protein kinase (MAPK) family.

Polypeptides that are normally not phosphorylatable can be modified to render them phosphorylatable (see U.S. Pat. No. 5,986,06).

III. Detection and Analysis of Protein Modifications and Modified Proteins

III.A. In General

The following are representative of teachings, compositions and methods of detecting and/or analyzing modified or unmodified proteins that can be used to practice the invention:

Jaquinod et al., "Mass Spectrometric Characterisation of Post-Translational Modification and Genetic Variation in Human Tetranectin", Biol Chem 380:1307-1314 (1999);

Kuster et al., "Identifying Proteins and Post-Translational Modifications by Mass Spectrometry" (review), Curr Opin Struct Biol. 8:393-400 (1998);

Kuster et al., "Glycosylation Analysis of Gel-Separated Proteins", Proteomics 1:350-361 (2001);

Yan et al., "Mass Spectrometric Determination of a Novel Modification of the N-terminus of Histidine-tagged Proteins Expressed in Bacteria", Biochem Biophys Res Commun 259:271-282 (1999);

Yamagata et al., "Mapping of Phosphorylated. Proteins on Two-Dimensional Polyacrylamide Gels Using Protein Phosphatase", Proteomics 2:1267-1276 (2002); Nilsson, "Analysis of Protein Glycosylation by Mass Spectrometry", Mol Biotechnol 2:243-280 (1994);

Kouach et al., "Application of Electrospray and Fast Atom Bombardment Mass Spectrometry to the Identification of Post-Translational and Other Chemical Modifications of Proteins and Peptides", Biol Mass Spectrom 23:283-294 (1994);

Han et al., "Post-Translational Chemical Modifications of Proteins—III. Current Developments in Analytical Procedures of Identification and Quantitation of Post-Translational Chemically Modified Amino Acid(s) and Its Derivatives", Int J Biochem 25:957-970 (1993); and Chen et al., published U.S. Patent Application 2003/0153007 (Automated Systems and Methods for Analysis of Protein Post-Translational Modification).

III.B. Amidation

The following are representative of teachings, compositions and methods of detecting and/or analyzing amidation that can be used to practice the invention: Jones et al., A Fluorometric Assay for Peptidyl Alpha-Amidation Activity Using High-Performance Liquid Chromatography, Anal Biochem 168:272-279 (1988).

III.C. Glycosylation and Deglycosylation

The following are representative of teachings, compositions and methods of detecting and/or analyzing glycosylation and/or deglycosylation that can be used to practice the invention:

Available from Prozyme:

FACE ® N-Linked Oligosaccharide Profiling Kit
GAG Set I Analytical Calibration Set
GAG Set II Analytical Calibration Set
Fucose Linkage Analysis Kit
Sialic Acid Linkage Analysis Kit
FACE ® N-Linked Oligosaccharide Profiling Kit
FACE ® Monosaccharide Composition Kit
FACE ® N-Linked Oligosaccharide Sequencing Kit III.D. Phosphorylation The following are representative of teachings, compositions and methods of detecting and/or analyzing phosphorylation that can be used to practice the invention: Kaufmann et al., Use of antibodies for detection of phosphorylated proteins separated by two-dimensional gel electrophoresis (review), Proteomics 1:194-199 (2001); Sickmann et al., Phosphoamino acid analysis (review), Proteomics 1:200-6 (2001); McLachlin et al., Analysis of phosphorylated proteins and peptides by mass spectrometry (review), Curr Opin Chem Biol. 5:591-602 (2001); and Reagan et al., published U.S. Patent Application 2003/0162230 (Method for Quantifying Phosphokinase Activity on Proteins).

IV. Applications

The at least partially homogeneous population of macromolecules of the present invention can be used for a number of applications, especially analytical applications, typically within biological sciences. The applications include, but are not limited to, electrophoresis, including for example gel electrophoresis and capillary electrophoresis, high-throughput screening, high pressure and low pressure liquid chromatography especially with gel filtration media, and ultracentrifugation. In one illustrative embodiment, the application that includes a homogenous molecular standard of the present invention is protein gel electrophoresis, especially SDS-polyacrylamide gel electrophoresis.

IV.A. Electrophoresis

Methods for separating (resolving) mixtures of macromolecules have applications such as scientific analysis (of, by way of non-limiting example, mixtures of proteins, as occurs in the field of proteomics), preparative techniques, diagnostic methods, regulatory analysis and the like. One non-limiting example of a method of resolving macromolecules (such as, by way of non-limiting example, nucleic acids, polypeptides and proteins) is electrophoresis.

Electrophoresis is a preparative and/or analytical method used to separate and characterize macromolecules. It is based on the principle that charged particles migrate in an applied electrical field. If electrophoresis is carried out in solution, molecules are separated according to their surface net charge density. If carried out in semisolid materials (gels), however, the matrix of the gel adds a sieving effect so that particles migrate according to both charge and size.

The invention is exemplified herein with regards to gel electrophoresis of macromolecules for analysis, purification or other manipulations thereof. The electrophoretic separation is performed by conventional methods according to the specific method, use, format or application.

The gel-based electrophoretic embodiments of the invention can be carried out in any suitable format, e.g., in standard-sized gels, minigels, strips, gels designed for use with microtiter plates and other high throughput (HTS) applications, and the like. Minigel and other formats include without limitation those described in the following patents and published patent applications: U.S. Pat. No. 5,578,180, to Engelhorn et al., entitled "System for pH-Neutral Longlife Electrophoresis Gel"; U.S. Pat. Nos. 5,922,185; 6,059,948; 6,096,182; 6,143,154; 6,162,338, all to Updyke et al.; published U.S. Patent Applications 20030127330 A1 and 20030121784 A1; and published PCT Application WO 95/27197, all entitled "System for pH-Neutral Stable Electrophoresis Gel"; U.S. Pat. No. 6,057,106, to Updyke et al., and published PCT application WO 99/37813, both entitled "Sample Buffer and Methods for High Resolution Gel Electrophoresis of Denatured Nucleic Acids"; U.S. Pat. No. 6,562,213 to Cabilly et al., and published PCT application WO 02/18901, both entitled "Electrophoresis Apparatus for Simultaneous Loading of Multiple Samples"; and published U.S. Patent Application 2002/0134680 A1, to Cabilly et al., and published PCT application WO 02/071024, both entitled "Apparatus and Method for Electrophoresis".

Protein electrophoresis can performed in the presence of a charged detergent like sodium dodecyl sulfate (SDS) which coats, and thus equalizes the charges of, most proteins, so that migration depends on size (molecular weight). Proteins are often separated in this fashion, i.e., SDS-PAGE (PAGE=polyacrylamide gel electrophoresis). In addition to SDS, one or more other denaturing agents, such as urea, can also be included in order to minimize the effects of secondary and tertiary structure on the electrophoretic mobility of proteins. Such additives are typically not necessary for nucleic acids, which have a similar surface charge irrespective of their size and whose secondary structures are generally broken up by the heating of the gel that happens during electrophoresis.

In general, electrophoresis gels can be either in a slab gel or tube gel form. For slab gels, the apparatus used to prepare them usually consists of two glass or plastic plates with a space disposed between them by means of a spacer or gasket material and the apparatus is held together by a clamping means so that the space created is closed on three sides and open at the top. A solution of unpolymerized gel-monomer is poured into the space while in its liquid state. A means of creating wells or depressions in the top of the gel (such as a comb) in which to place samples is then placed in the space. The gel-monomer solution is then polymerized and becomes a solid gel. After polymerization is complete, the comb device is removed and the gel, while still held within the plates, is then ready for use. Examples of such apparatus are well known and are described in U.S. Pat. No. 4,337,131 to Vesterberg; U.S. Pat. No. 4,339,327 to Tyler; U.S. Pat. No. 3,980,540 to Hoefer et al.; U.S. Pat. No. 4,142,960 to Hahn et al.; U.S. Pat. No. 4,560,459 to Hoefer; and U.S. Pat. No. 4,574,040 to Delony et al. Tube gels are produced in a similar manner, however, instead of glass or plastic plates, glass capillary tubing is used to contain the liquid gel.

Two commonly used media for gel electrophoresis and other separation techniques are agarose and polyacrylamide. Each of these is described in turn as follows.

IV.A.1. Agarose

Agarose is a colloidal extract prepared from seaweed. Different species of seaweed are used to prepare agarose; commercially available agarose is typically prepared from genera including, but not limited to, *Gracilaria*, *Gelidium*, and *Pterocladia*. It is a linear polysaccharide (average molecular mass of about 12,000) made up of the basic repeat unit agarobiose, which comprises alternating units of galactose and 3,6-anhydrogalactose. Agarose contains no charged groups and is thus useful as a medium for electrophoresis.

Agarose gels have a very large "pore" size and are used primarily to separate large molecules, e.g., those with a molecular mass greater than about 200 kDa. Agarose gels can be prepared, electrophoresed ("run") and processed faster than polyacrylamide gels, but their resolution is generally inferior. For example, for some macromolecules, the bands formed in agarose gels are "fuzzy" (diffuse). The concentration of agarose typically used in gel electrophoresis is between from about 1% to about 3%.

Agarose gels are formed by suspending dry agarose in an aqueous, usually buffered, media, and boiling the mixture until a clear solution forms. This is poured into a cassette and allowed to cool to room temperature to form a rigid gel.

IV.A.2. Polyacrylamide

Acrylamide polymers are used in a wide variety of chromatographic and electrophoretic techniques and are used in capillary electrophoresis. Polyacrylamide is well suited for size fractionation of charged macromolecules such as proteins and nucleic acids (e.g., deoxyribonucleic acids, a.k.a. DNA, and ribonucleic acids, a.k.a. RNA).

The creation of the polyacrylamide matrix is based upon the polymerization of acrylamide in the presence of a crosslinker, usually methylenebisacrylamide (bis, or MBA). Upon the introduction of catalyst, the polymerization of acrylamide and methylene bisacrylamide proceeds via a free-radical mechanism. The most common system of catalytic initiation involves the production of free oxygen radicals by ammonium persulfate (APS) in the presence of the tertiary aliphatic amine N,N,N',N'-tetramethylethylenediamine (TEMED).

In the case of acrylamide, various chemical polymerization systems may be used. For example, TEMED and persulfate may be added to provide polymerization initiation. Once the temperature becomes stable or approaches ambient temperature, the polymerization is assumed to be complete. If desired, an acrylamide gradient may be developed by successively adding solutions with increasing amounts of acrylamide and/or cross-linking agent. Alternatively, differential initiation may be used, so as to provide varying degrees of polymerization and thus prepare a gradient gel.

Electrophoretic gels based on polyacrylamide, are produced by co-polymerization of monoolefinic monomers with di- or polyolefinic monomers. The co-polymerization with di- or polyfunctional monomers results in cross-linking of the polymer chains and thereby the formation of the polymer network. As monoolefinic monomers used in the invention can be mentioned acrylamide, methacrylamide and derivatives thereof such as alkyl-, or hydroxyalkyl derivates, e.g. N,N-dimethylacrylamide, N-hydroxypropylacrylamide, N-hydroxymethylacrylamide. The di- or polyolefinic monomer is preferably a compound containing two or more acryl or methacryl groups such as e.g. methylenebisacrylamide, N,N-diallyltartardiamide, N,N'-1,2-dihydroxyethylene-bisacrylamide, N,N-bisacrylyl cystamine, trisacryloyl-hexahydrotriazine. In a broader sense, "polyacrylamide gels" also include gels in which the monoolefinic monomer is selected from acrylic- and methacrylic acid derivatives, e.g., alkyl esters such as ethyl acrylate and hydroxyalkyl esters such as 2-hydroxyethyl methacrylate, and in which cross-linking has been brought about by means of a compound as mentioned before. Further examples of gels based on polyacrylamide are gels made by co-polymerization of acrylamide with a polysaccharide substituted to contain vinyl groups, for example allyl glycidyl dextran as described in EP 87995. The gels used in the invention are prepared from an aqueous solution containing 2-40% (w/w), preferably 3-25% (w/w) of the monomers mentioned above. The amount of cross-linking monomer is about 0.5% to about 15%, preferably about 1% to about 7% by weight of the total amount of monomer in the mixture.

In addition to the initiator and monomers the reaction mixture may contain various additives, the choice of which will depend on the particular electrophoretic technique contemplated. Thus, for isoelectric focusing a certain type of amphoteric compounds are added which will create a pH gradient in the gel during electrophoresis. Or a gradient of buffering compounds bearing vinyl groups can be copolymerized into the gel so as to create an immobilized pH gradient.

IV.A.3. Composite Gels

Composite gels, formed from two or more electrophoretic media, can also be used. Non-limiting examples of polyacrylamide-agarose compositions include those described in the following non-comprehensive list: U.S. Pat. No. 5,785,832 to Chiari et al., entitled "Covalently Cross-Linked, Mixed-Bed Agarose-Polyacrylamide Matrices for Electrophoresis and Chromatography"; Andrews, "Electrophoresis on Agarose and Composite Polyacrylamide-Agarose Gels", Electrophoresis, Clarendon Press, pg. 148-177 (1986); Bates et al., "Autonomous parvovirus LuIII encapsidates equal amounts of plus and minus DNA strands" J. Virol. 49:319-324 (1984); Dahlberg et al., "Electrophoretic Characterization of Bacterial Polyribosomes in Agarose-Acrylamide-Composite Gels", J. Mol. Biol. 41:139-147 (1969); Fisher et al., "Role of Molecular Conformation in Determining the Electrophoretic Properties of Polynucleotides in Agarose-Acrylamide Composite Gels", Biochemistry 10:1895-1899 (1971); Horowitz et al., "Electrophoresis of Proteins and Nucleic Acids on Acrylamide-Agarose Gels Lacking Covalent Cross-Linkings", Anal. Biochem. 143:333-340 (1984); Isono et al., "Lack of ribosomal protein S1 in Bacillus stearothermophilus" Proc Natl Acad Sci USA 73:767-770 (1976); Peacock et al., "Molecular Weight Estimation and Separation of Ribonucleic Acid by Electrophoresis in Agarose-Acrylamide Composite Gels," Biochemistry 7:668-674, (1968); Rashid et al., "Electrophoretic Extraction-Concentration of Ribonucleic Acid from Agarose-Acrylamide Composite Gels", Anal Biochem 127:334-339 (1982); and Ringborg et al., "Agarose-Acrylamide Composite Gels for Microfractionation of RNA", Nature 220:1037-1039 (1968).

IV.A.4. Representative Gels

Any suitable gel and buffers can be used to practice the invention. Non-limiting examples of gels and buffers include those described herein and in the following: U.S. Pat. No. 5,578,180, to Engelhorn et al., entitled "System for pH-Neutral Longlife Electrophoresis Gel"; U.S. Pat. Nos. 5,922,185; 6,059,948; 6,096,182; 6,143,154; 6,162,338, all to Updyke et al.; published U.S. Patent Applications 20030127330 A1 and 20030121784 A1; and published PCT Application WO 95/27197, all entitled "System for pH-Neutral Stable Electrophoresis Gel"; U.S. Pat. No. 6,057,106, to Updyke et al., and published PCT application WO 99/37813, both entitled "Sample Buffer and Methods for High Resolution Gel Electrophoresis of Denatured Nucleic Acids"; U.S. Pat. No. 6,562,213 to Cabilly et al., and published PCT application WO 02/18901, both entitled "Electrophoresis Apparatus for Simultaneous Loading of Multiple Samples"; Published U.S. Patent Application 20020134680 A1, to Cabilly et al., and published PCT application WO 02/071024, both entitled "Apparatus and Method for Electrophoresis"; and U.S. Pat. No. 5,785,832, to Chiari et al., entitled "Covalently Cross-Linked, Mixed-Bed Agarose-Polyacrylamide Matrices for Electrophoresis and Chromatography."

IV.A.5. Isoelectric Focusing (IEF).

One type of electrophoresis is usually referred to as isoelectric focusing (IEF) or electrofocusing. IEF, which can be carried out in an electrophoretic medium or in solution, involves passing a mixture through a separation medium which contains, or which may be made to contain, a pH gradient or other pH function. The device or gel has a relatively low pH at one end, while at the other end it has a higher pH. IEF is discussed in various texts such as Isoelectric Focusing by P. G. Righetti and J. W. Drysdale (North Holland Publ., Amsterdam, and American Elsevier Publ., New York, 1976).

The charge on a protein or other molecule depends on the pH of the ambient solution. At the isoelectric point (pI) for a certain molecule, the net charge on that molecule is zero. At a pH above its pi, the molecule has a negative charge, while at a pH below its pI the molecule has a positive charge. Each different molecule has a characteristic isoelectric point. When a mixture of molecules is electrophoresed in an IEF system, an anode (positively charged) is placed at the acidic end of the system, and a cathode (negatively charged) is placed at the basic (alkaline) end. Each molecule having a net positive charge under the acidic conditions near the anode will be driven away from the anode. As they electrophorese through the IEF system, molecules enter zones having less acidity, and their positive charges decrease. Each molecule will stop moving when it reaches its particular pI, since it no longer has any net charge at that particular pH. This effectively separates molecules that have different pI values. The isolated molecules of interest can be removed from the IEF device by various means, or they can be stained or otherwise characterized.

Some types of IEF systems generate pH gradients by means of "carrier ampholytes." These are synthetic ampholytes that often have a significant amount of buffering capacity. When placed in an IEF device, each carrier ampholyte will seek its own isoelectric point. Because of their buffering capacity, many carrier ampholytes will establish a pH plateau rather than a single point. By using a proper mixture of carrier ampholytes, it is possible to generate a relatively smooth pH gradient for a limited period of time. Such mixtures are sold commercially under various trade names, such as Ampholine (sold by LKB-Produkter AB of Bromma, Sweden), Servalyt (sold by Serva Feinbiochemica of Heidelberg, FRG), and Pharmalyte (sold by Pharmacia Fine Chemicals AB, Uppsala, Sweden). The chemistry of ampholyte mixtures is discussed in various references, such as U.S. Pat. No. 3,485,736; Matsui et al., Methods Mol. Biol. 112:211-219 (1999); and Lopez, Methods Mol. Biol. 112: 109-110 (1999).

In IEF in Immobilized pH gradients (IPG), amphoteric ions are forced to reach a steady-state position along pH inclines of various scopes and spans (see Righetti et al., Electrophoresis 15:1040-1043, 1994; Righetti et al., Methods Enzymol. 270: 235-255, 1996; and 2-D Electrophoresis using immobilized pH gradients—Principles and Methods, Edition AC, Berkelman, T. and T. Stenstedt, Amersham Biosciences, Freiburg, Germany, 1998.). In one popular version of IPG, the pH gradient is in the form of a strip and is referred to as a "strip gel" or a "gel strip" that can be used in appropriate formats. See, by way of non-limiting example, published PCT patent applications WO 98/57161 A1, WO 02/09220 A1, published U.S. patent application US 2003/0015426 A1, and U.S. Pat. Nos. 6,599,410; 6, 156,182; 6,113,766; and 6,495,017.

IV.A.6. Two-Dimensional Electrophoresis

Two-dimensional (2D) electrophoresis techniques are also known and involve a first electrophoretic separation in a first dimension, followed by a second electrophoretic separation in a second, transverse dimension. In a common 2D electrophoretic method, proteins are subjected to IEF in a polyacrylamide gel in the first dimension, resulting in separation on the basis of isoelectric point (pI), and are then subjected to SDS-PAGE in the second dimension, resulting in further separation on the basis of size (O'Farrell, J. Biol. Chem. 250:4007-4021, 1975).

IV.A.7. Staining Gels

A typical method for staining electrophoretic media in a gel format that can be carried out at ambient temperature includes the steps of fixing the gel (e.g., incubating the gel in an aqueous solution having about 40% ethanol and about 10% acetic acid for about 1 hour); rinsing the fixed gel one or more times with distilled water for about 10 minutes; incubating the gel in a staining solution for about 1 hour; and washing the gel one or more times with water or a buffer, such as one comprising sodium phosphate at a concentration of from about 5 to about 100 mM, e.g., 5, 10, 15, 20, 25, or 50 mM, the buffer having a pH of from about 6 to about 8, e.g., 7.0, 7.1, 7.2, 7.3, 7.4, 7.5, 7.6, 7.7, 7.8 or 7.9.

IV.B. Capillary Electrophoresis (CE)

Electrophoresis also includes techniques known collectively as capillary electrophoresis (CE). Capillary electrophoresis (CE) achieves molecular separations on the same basis as conventional electrophoretic methods, but does so within the environment of a narrow capillary tube (25 to 50 μm). The main advantages of CE are that very small (nanoliter) volumes of sample are required; moreover, in a capillary format, separation and detection can be performed rapidly, thus greatly increasing sample throughput relative to gel electrophoresis. Some non-limiting examples of CE include capillary electrophoresis isoelectric focusing (CE-IEF) and capillary zone electrophoresis (CZE).

Capillary zone electrophoresis (CZE) is a technique that separates molecules on the basis of differences in mass to charge ratios, which permits rapid and efficient separations of charged substances (for a review, see Dolnik, Electrophoresis 18:2353-2361, 1997). In general, CZE involves introduction of a sample into a capillary tube, i.e., a tube having an internal diameter from about 5 to about 2000 microns, and the application of an electric field to the tube. The electric potential of the field both pulls the sample through the tube and separates it into its constituent parts. Each constituent of the sample has its own individual electrophoretic mobility; those having greater mobility travel through the capillary tube faster than those with slower mobility. As a result, the constituents of the sample are resolved into discrete zones in the capillary tube during their migration through the tube. An on-line detector can be used to continuously monitor the separation and provide data as to the various constituents based upon the discrete zones.

CZE can be generally separated into two categories based upon the contents of the capillary columns. In "gel" CZE, the capillary tube is filled with a suitable gel, e.g., polyacrylamide gel. Separation of the constituents in the sample is predicated in part by the size and charge of the constituents traveling through the gel matrix. This technique, sometimes referred at as capillary Gel Electrophoresis (CGE), is described by Hjertñĭ (J. Chromatogr. 270:1, 1983), and is suitable for resolving macromolecules that differ in size but have a constant charge-to-mass ratio (Guttman et al., Anal. Chem. 62:137, 1990).

In "open" CZE, the capillary tube is filled with an electrically conductive buffer solution. Upon ionization of the capillary, the negatively charged capillary wall will attract a layer of positive ions from the buffer. As these ions flow towards the cathode, under the influence of the electrical potential, the bulk solution (the buffer solution and the sample being analyzed), must also flow in this direction to maintain electroneutrality. This electroendosmotic flow provides a fixed velocity component which drives both neutral species and ionic species, regardless of charge, towards the cathode. Fused silica is principally utilized as the material for the capillary tube because it can withstand the relatively high voltage used in CZE, and because the inner walls of a fused silica capillary ionize to create the negative charge which causes the desired electroendosmotic flow. The inner wall of the capillaries used in CZE can be either coated or uncoated. The coatings used are varied and known to those in the art. Generally, such coatings are utilized in order to reduce adsorption of the charged constituent species to the charged inner wall. Similarly, uncoated columns can be used. In order to prevent such adsorption, the pH of the running buffer, or the components within the buffer, are manipulated.

IV.C. High-Throughput Screening (HTS)

In some embodiments, electrophoresis is carried out in formats suitable for high-throughput screening (HTS). Preferred HTS formats, as well as other formats for other electrophoretic applications, are described in: U.S. Pat. No. 6,562,213 to Cabilly et al., and published PCT application WO 02/18901, both entitled "Electrophoresis Apparatus for Simultaneous Loading of Multiple Samples"; U.S. Pat. No. 6,379,516 and published U.S. patent application Ser. 20020134680 A1, both to Cabilly et al., and published PCT application WO 02/071024, all entitled "Apparatus and Method for Electrophoresis"; and U.S. Pat. Nos. 5,582,702; 5,865,974; and 6,379,516, all to Cabilly et al., and published PCT applications WO 96/34276 and WO 97/41070, all entitled "Apparatus and Method for Electrophoresis."

IV.D. Kits

In some embodiments, the homogeneous populations of molecules of the invention are prepared as solutions to be used in kits and methods such as electrophoresis. In certain examples, such solutions are provided "ready to go", i.e., they can be used directly in gels without further manipulation. Alternatively, a stock solution is provided and is diluted to prepare a molecular standard. Moreover, the molecules of the molecular standard can be provided in separate containers that are mixed together in order to prepare a molecular standard.

In one embodiment, provided herein is a kit comprising an isolated high molecular weight standard. Furthermore, the kit can include a molecular weight protein standard that is not a high molecular weight protein standard. For example, the kit can include protein standards that are less than 250 kDa, as illustrated in the Examples herein. In certain aspect of the invention, the protein standards are pre-stained standards. Furthermore, the kit can include a set of protein standards, for example, 2, 3, 4, 5, 6, 7, 8, 9, 10, 11, 12, 13, 14, 15, or 20 protein standards. At least 2, 3, 4, 5, 6, 7, 8, 9, or 10 of the protein standards can be high molecular weight protein standards.

Liquid components of kits are stored in containers, which are typically resealable. A preferred container is an Eppendorf tube, particularly a 1.5 ml Eppendorf tube. A variety of caps may be used with the liquid container. Generally preferred are tubes with screw caps having an ethylene propylene O-ring for a positive leak-proof seal. A preferred cap uniformly compresses the O-ring on the beveled seat of the tube edge. Preferably, the containers and caps may be autoclaved and used over a wide range of temperatures (e.g., +120° C. to −200° C.) including use with liquid nitrogen. Other containers can be used. Kits of the invention in certain aspects, are stored at −20 C or below.

Kits of the invention can further comprise one or more sets of instructions.

Kits of the invention can further comprise one or more calibration or other guides that shows one or more images of the molecular standards after they have been subject to a condition or process of interest, such as gel electrophoresis. Typically, such guides will indicate a value for each member of the molecular standard and its correlation or relationship with a molecular characteristic. For example, a guide for electrophoresis might show a gel on which a protein or DNA "ladder" has been electrophoresed and the molecular weights corresponding to each band in the image.

A kit of the invention that is designed to be used to calibrate an instrument or machine may have different sets of instructions and be called a "Calibration Kit." Such a kit may further include reagents or other compositions for the operation of the instrument or machine during calibration procedures or otherwise, such as solutions and devices for flushing lines, for rinsing gel matrices, or for cleaning sensors such as image scanners and optical or fluorescent viewers; instructions, which may be in the form of software, for running a calibration program on the instrument or machine; and the like.

IV.E. Pre-Stained High Molecular Weight Markers

In some embodiments of the present invention, molecular standards are pre-stained to facilitate their detection. "Pre-stained" markers, as used herein, refers to marker molecules that are coupled to molecules of a detectable substance, such as dyes that are visible or fluorescent, prior to being loaded onto an electrophoretic gel or other separation medium or apparatus. Such pre-stained markers may be detected before, during or after electrophoresis without the need for a separate staining step. In some embodiments, the pre-stained molecular standards are pre-stained protein standards. In some embodiments, the pre-stained protein standards comprise high molecular weight proteins, e.g. proteins with molecular weights greater than 300 kDa.

In some embodiments of the present invention, one or more species of pre-stained molecular standards, e.g. pre-stained protein standards, are included in a kit. Some such kits are comprised of high molecular weight pre-stained protein standards.

EXAMPLES

The following Examples are included herewith for purposes of illustration only and are not intended to be limiting of the invention.

Example 1: Laminin Polypeptides
Example 2: Deglycosylation of Laminin
Example 3: Reduction and Alkylation of Laminin
Example 4: Mass Spectrometry
Example 5: Apparent Molecular Weight
Example 6: Preparation of a Set of Protein Standards
Example 7: Kit Instructions
Example 8: De-Phosphorylation
Example 9: Dna Methylation
Example 10: Pre-Stained Laminin
Example 11: Pre-Stained β-Galactosidase
Example 12: HiMark™ Pre-stained Standards A listing of some of the chemicals and reagents used in the Examples, and the suppliers of those chemicals and reagents, is as follows.

| Chemical or Reagent | Supplier |
|---|---|
| Iodoacetamide | Sigma |
| Dithiothreitol (DTT) | Sigma |
| α-cyano-4-hydroxycinnamic acid | Aldrich |
| Acetonitrile | Aldrich |
| Trypsin | Promega |
| Fibronectin | Calbiochem |
| DNA-Dependent Kinase | Promega |
| Normal human serum | Sigma |
| Normal rat serum | Sigma |
| 3-8% Tris-Acetate (TA) Gels | Invitrogen |
| 4% Tris-Glycine (TG) Gels | Invitrogen |
| 4-12% NUPGE ® Gels | Invitrogen |
| Ammonium bicarbonate | Sigma |
| Protease Inhibitor Cocktail I | Calbiochem |
| Protease Inhibitor Cocktail III | Calbiochem |
| PNGase F | New England Biolabs |
| Endo-O-Glycosidase | ProZyme |
| Laminin Natural Mouse | Invitrogen |
| Sialidase A | ProZyme |
| 20% SDS | Invitrogen |
| Triton X100 | Sigma |
| 100 kD Ultra-concentrators | Amicon |
| Tri-n-butylphosphine (TBP) | Aldrich |
| Isopropanol | Acros |
| Dialysis membrane 12 kDa MWCO | Invitrogen |
| Iodoacetic Acid | Sigma |

Example 1

Laminin Polypeptides

Laminin is a protein found in the basement membrane, and consists of three peptide chains that are linked by disulfide bonds. There are several different types of laminin that vary in molecular weight. See, e.g., Miner et al., The laminin alpha chains: expression, developmental transitions, and chromosomal locations of alpha1-5, identification of heterotrimeric laminins 8-11, and cloning of a novel alpha3 isoform, J Cell Biol 137:685-701 (1997); Teller et al., Interactions between laminin and epithelial cells in intestinal health and disease. Exp. Rev. Mol. Med. 28 Sep. 2001 (available on the internet at ermm.cbcu.cam.ac.uk/01003623h.htm; and Simon-Assmann et al., The laminins: role in intestinal morphogenesis and differentiation. Ann N Y Acad. Sci. 859:46-64 (Review) (1998).

Unless indicated otherwise, Laminin type 1 from Engelbreth-Holms-Swarm (EHS) sarcoma grown in mouse was used in the Examples. Laminin type 1 consists of three polypeptide chains: alpha 1 (335,732 Da), beta 1 (194,670 Da) and gamma 1 (173,999 Da). The protein is glycosylated and contains many cysteines in disulfide bridges.

Commercially available laminin is sold by Invitrogen (Carlsbad, Calif.), BD Biosciences (San Jose, Calif.), Serva (Heidelberg, Del.) and other companies as a 800 kilodalton (kDa) to 1000 kDa protein that comprises three polypeptide chains. The largest chain has a molecular weight of 400 kDa. A search on the Swiss-Prot database revealed that the alpha 5 chain from mice has a molecular weight of 404 kilodaltons (kDa).

Example 2

Deglycosylation of Laminin

Deglycosylation: 1 mg of laminin stock solution was mixed with 6.25 µl of 20% SDS and 31.25 µl of 2 M DTT, mixed well and incubated at room temperature for 30 minutes. Then, 65 µl of 14% Triton X-100 was added and the protein solution was mixed well. 5 µl PNGase F (New England Biolabs) was added and the protein solution was mixed well and was left at 4° C. for 48 to 72 hours.

Purification: 2 ml of 50 mM Tris pH=8, 0.1% SDS buffer was added to 1 ml of deglycosylated laminin solution. The protein was concentrated by centrifugation at 3,000×g using a filter having a molecular weight cut-off (MWCO) of 100 kDa MWCO (Amicon, Beverly, Mass.) until the sample volume was between 0.5 to 1 ml. This protocol was repeated two more times, with 2 ml buffer being added each time. After the last concentration cycle, the protein concentration was adjusted to 1 mg/ml if needed by adding 50 mM Tris, 0.1% SDS buffer to the solution.

FIG. 4A is an image of a 3-8% Tris-Acetate gel on which has been electrophoresed, in lane 1, laminin deglycosylated with PNGase F and, in lane 2, untreated laminin. As can be seen in FIG. 4A, the treated laminin shows how the laminins bands become sharper (more tightly resolved), and that there is a shift in apparent molecular weight. Also in FIG. 4A, lane 1, it can be seen that the beta- (middle band) and gamma- (lowest band) chains of the laminin, which otherwise blend together (compare to lane 2 of FIG. 4A), have been cleanly separated.

Example 3

Reduction and Alkylation of Laminin

Reduction and Alkylation: 100 µl of 20% SDS was added to the 1 ml of 1 mg/ml deglycosylated laminin solution and the sample was incubated at room temperature for 1 hour. Then, 40 µl 200 mM tri-n-butylphosphine (TBP) in isopropanol was added and the sample was vortexed for 10 seconds. Then the sample was left in a vortexer 1 hour. After the addition of the TBP the sample became cloudy but, by the end of the incubation, the sample solution was clear. Then, 100 µl 1 M iodoacetic acid pH=7 in 25 mM phosphate was added to the protein sample, which was incubated for 1 hour at room temperature.

Purification: 2 ml of 50 mM Tris pH=0.8, 1% SDS buffer was added to 1 ml alkylated laminin solution. The protein was concentrated by centrifugation at 3,000×g using a filter having a 100 kDa MWCO (Amicon) until the sample volume was between 0.5 to 1 ml. This protocol was repeated two more times, with 2 ml buffer being added each time. After the last concentration cycle, the protein concentration was adjusted to 1 mg/ml if needed by adding 50 mM Tris, 0.1% SDS buffer to the solution.

Laminin treated as above is, in some instances, referred to hereinafter as "modified laminin."

Example 4

Mass Spectrometry

10 µl of the reduced and alkylated sample was loaded onto SDS-PAGE gels. After the electrophoretic run, the gels were stained with SIMPLYBLUE™ safe stain and then destained in water for 1 to 2 hours at room temperature. Portions of the gels comprising the protein bands were cut out with a razor blade and placed in 1.5 ml tubes. The gel fragments were destained with two additions of 500 µl of 30% acetonitrile in 25 mM ammonium bicarbonate pH=8, vortexing for 15 min after each addition. The gel bands were dehydrated with addition of 300 µl 100% acetonitrile and dried on a SPEEDVAC® concentrator system for 5 minutes. Then 10 µl 20 ng/µl Trypsin in 25 mM ammonium bicarbonate was added to each gel band. The samples were incubated for 30 min at room temperature and 20 µl 25 mM ammonium bicarbonate was added to each gel band and the samples were left at 37° C. for 16-18 hours for digestion. After digestion the liquid in the tubes was transferred to a clean 1.5 ml tube. The gel fragments were extracted with 100 µl of 0.1% trifluoroacetic acid (TFA) for 30 minutes. A second extraction was done with 100 µl of 50% acetonitrile/0.05% TFA, and all the extracts were pooled. The extracts were dried using a SPEEDVAC® concentrator system (Savant, Holbrook, N.Y.), and 5 µl 0.1% TFA was added to each tube. Then 3 µl of each sample was mixed with 7 µl of 10 mg/ml alpha-cyano-4-hydroxycinnamic acid (CHCA) in 50% acetonitrile/0.05% TFA. One microliter was loaded on the MALDI target. The analyses were done using a Voyager DE STR mass spectrometer (Applied Biosystems, Foster City, Calif.).

This mass spectrometry analysis by peptide mapping revealed that Invitrogen's laminin 1 has a large alpha 1 chain with a molecular weight of 338 kDa. According to the Swiss-Prot database, a signal peptide with length of 24 amino acids is removed after expression, so the mature protein size is 335,732 Da The protein was identified as laminin 1 with very high confidence over a range of coverage of the protein's amino acid sequence, including the N-terminus and C-terminus of the protein.

Example 5

Apparent Molecular Weight

The apparent molecular weight of the modified laminin was estimated based on a standard curve prepared using proteins with known molecular weights. The following protein samples were loaded on each gel: Mark 12 Unstained Standard, BENCHMARK™ Protein Standard, Precision Plus, Normal human serum, Normal rat serum, DNA-dependent Kinase, Fibronectin, and High Molecular Weight Unstained Standard. The molecular weight standards were loaded directly without any preparation.

The serum samples were prepared the following way: To 750 µl centrifuge tube 20 µl serum, 25 µl 4×LDS Sample buffer, 5 µl 2M DTT and 50 µl water were added. The samples were reduced at 70° C. for 10 min.

The DNA-dependent kinase sample was prepared by adding 8.3 µl 4×LDS and 1.6 µl 2M DTT to the tube (with 25 µl protein solution) and reducing for 10 min at 70° C.

Fibronectin was prepared by adding 20 µl fibronectin solution (500 µg/ml), 25 µl 4×LDS, 5 µl DTT and 50 µl water to 750 µl centrifuge tube and reducing for 10 min at 70° C.

The samples were loaded on 4% TG (Tris-Glycine), 3-8% TA (Tris-Acetate) and 4-12% NUPAGE®/MOPS gels. The gels were stained with Coomassie R250 and destained with multiple washes with 8% acetic acid.

The molecular weights of the laminin polypeptide chains calculated by their sequence are: alpha 1-335,732 Da, beta 1-194,670 Da and gamma 1-173,999 Da. However, in these experiments, laminin polypeptide chains alkylated with iodine acetic acid protein runs as if it had a higher apparent molecular weight. The gamma 1 chain runs larger than myosin (224 kDa) on a 3-8% TA gel when alkylated with iodine acetic acid. The other laminin chains also seem to run as larger apparent molecular weight bands.

Without wishing to be bound by any particular theory, this is probably due to the addition of very large number of negative charges to the protein when alkylated with iodine acetic acid. There are 163 cysteines in the alpha chain, 127 cysteines in the beta chain and 99 cysteines in the gamma chain of the laminin. When the protein is alkylated with iodine acetic acid, the corresponding number of negative charges are added to each polypeptide chain. It is possible that the highly negatively charged molecule binds different number of SDS molecules and has different hydrodynamic radius. Therefore it migrates differently to its true molecular weight. A change of the migration rate was not observed for the polypeptide chains of laminin when the protein is alkylated with iodoacetamide, probably because the charge of the protein has not changed much, if at all, when alkylated with non-ionic alkylation reagent.

In order to establish the apparent molecular weight with which this protein migrates in specific electrophoretic conditions, the following experiments were carried out.

The estimation of the molecular weight of proteins is normally done by constructing a calibration curve based on proteins with known molecular weights and calculating the molecular weight of the unknown protein based on that curve. Since there are no existing molecular weight standards with suitable molecular weights, several proteins from human and rat serum with molecular weight in the desired range were identified.

One protein from human serum—apolipoprotein B-100 precursor—was identified and has a molecular weight of 516 kDa according to the protein sequence in the Swiss-Prot database (Accession #P04114). According to the Swiss-Prot database, a signal peptide with length of 27 amino acids is removed after expression, and the final molecular weight of the mature protein is 512 kDa. The protein identification was done multiple times with high confidence of the identification and well distributed peptide coverage map that spans from the N-terminus to nearly the C-terminus of the protein and confirmed that the identity of the complete (unprocessed) version of the protein.

Also identified was one protein from rat serum: rat plectin, having a molecular weight of 533 kDa (Accession #P30427). A peptide coverage map was prepared and shows that the identified peptides cover the sequence from the first few residues to nearly the C-terminus of the protein.

A commercially available protein—human DNA-dependent kinase—was purchased from Promega (Madison, Wis.). According to the sequence of this protein found at the Swiss-Prot database (Accession #P78527) the molecular weight of the largest subunit of the protein is 469 kDa.

Rat fibronectin was purchased from Calbiochem (San Diego, Calif.). According to the sequence information obtained from the Swiss-Prot database (Accession #PO4937), the molecular weight of the protein was calculated to be 269 kDa after cleavage of 32 amino acids signal peptide.

These four high molecular weight proteins—rat plectin (533 kDa), human apolipoprotein B-100 precursor (516 kDa), human DNA-dependent kinase (469 kDa), and rat fibronectin (269 kDa)—together with other molecular weight standards as described herein, were run (electrophoresed) on 4% TG, 3-8% TA, 7% TA and 4-12% NUPAGE®/ MOPS gels with 1×MOPS running buffer.

After running on SDS-PAGE gels, the Rf values of all resolved bands from each molecular weight standard (Mark 12, Magic Mark, Bench Mark and Precision Plus), rat fibronectin, apolipoprotein B-100, rat plectin and human DNA-dependent kinase were measured using the Alpha Innotech imaging system. The molecular weights of the proteins and the Rf values measured on the Alpha Innotech imaging system were entered in an Excel spreadsheet and the $\log_{10}$ (MW) values were calculated. Scatter plots of $\log_{10}$ MW v/s Rf were prepared and trendlines with R2 closest to 1 were selected.

The $\log_{10}$ MW values of the laminin polypeptide chains were calculated using the equations describing the trendline (x=Rf, y=$\log_{10}$ MW). The molecular weight (MW) of the polypeptide chains were calculated using the equation: MW=$10^y$.

The apparent molecular weight of the alpha chain of laminin was calculated to be 490 kDa. This corresponds well with the migration of the alpha chains on the gels (i.e. higher than the DNA-dependent kinase and just below the apolipoprotein B-100). Close examination of the migration of the beta and gamma chains of the laminin reveals similar situation. The calibration of these polypeptide chains is also more accurate (representing better the migration of the protein on the gel relative to standards with close molecular weight). Therefore, this method for calibration of the laminin polypeptide chains was used on all of the gel types that were tested.

Using the trendline equations from the corresponding charts the molecular weights of the laminin bands were calculated and are as follows:

| Polypeptide | 4% TG | 3-8% TA | 7% TA | 4-12% NuPAGE |
|---|---|---|---|---|
| Laminin alpha | 515 kDa | 507 kDa | 490 kDa | 448 kDa |
| Laminin beta | 365 kDa | 298 kDa | 280 kDa | 226 kDa |
| Laminin gamma | 272 kDa | 247 kDa | 227 kDa | 220 kDa |

Although the molecular weights of the laminin polypeptide chains are: alpha 1 (335,732 Da), beta 1 (194,670 Da) and gamma 1 (173,999 Da) the apparent molecular weights (the molecular weight that these polypeptides migrate with on electrophoresis gel) are different.

Example 6

Preparation of a Set of Protein Standards

The following proteins were used for the preparation of a set of protein standards (a.k.a. as a "protein ladder") that is sometimes hereinafter referred to as the Unstained High Molecular Weight Standard (UHMWS).

The set of standards comprises the proteins listed in the following table:

| Protein | Apparent Molecular Weight (kDa) |
|---|---|
| Laminin - alpha chain | 500 |
| Laminin - beta chain | 290 |
| Laminin - gamma chain | 240 |
| 160 kDa recombinant protein | 160 |
| B-galactosidase | 116 |
| Phosphorylase-b | 97 |
| BSA | 66 |
| GDH | 55 |
| 40 kDa recombinant protein | 40 |

All proteins except laminin are stock solutions from the MARK12™ or BENCHMARK™ standards (Invitrogen, Carlsbad, Calif.) (Flynn et al., Protein Analysis with the BENCHMARK™ Protein, Focus 19:33-35 (1997), incorporated herein by reference in its entirety).

An image showing the molecular weight standard, comprising the laminin subunits (the upper three bands) that have been deglycosylated and reduced and alkylated, after electrophoresis in a 3-8% Tris-Acetate gel and staining is shown in FIG. 4B.

The CF (Concentration Factor—the amount of stock solution needed to make 1 ml of Unstained High Molecular Weight Standard) of modified laminin was determined by running dilutions of the concentrated stock solution side by side with pre-qualified high molecular weight standard on 3-8% TA gel. The dilution that matches the bend intensity of the standard was used to determine the CF factor. The CF factors of other proteins were typically determined when the stock solutions were prepared.

All proteins were blended according to their CF factors and the needed volume water and NuPAGE® LDS Sample buffer was added to achieve 1× concentration. The final formulation of the standard was stored at −20° C.

Example 7

Kit Instructions

Exemplary instructions for a kit and/or associated equipment and solutions of the invention are set forth in this Example.

The Unstained High Molecular Weight (HMW) Protein Standard allows accurate molecular weight estimation of high molecular weight proteins on, e.g., NUPAGE® NOVEX® Tris-Acetate Gels with Tris-Acetate SDS buffer system. A number of features of the standard are: it consists of 9 protein bands in the range of 40-500 kDa; it is designed particularly but not exclusively for use with NUPAGE® NOVEX® 3-8% and 7% Tris-Acetate Gels under denaturing conditions; it is supplied in a ready-to-use format; it is optionally visualized with Coomassie protein stain or silver staining; and it is optionally visualized also with Ponceau S, Coomassie protein stain, or other membrane stains after western transfer.

In one embodiment, 250 ml of HIMARK™ Unstained High Molecular Weight Protein Standard is supplied in a storage buffer comprising 250 mM Tris-HCl, pH 8.5; 0.5 mM EDTA; 50 mM DTT; 10% glycerol; 2% LDS; 0.2 mM Coomassie protein stain G-250; and 0.175 mM Phenol red, and stored at −20° C., under which conditions the Standard is stable for 6 months. Repeated freezing and thawing are avoided.

In one embodiment, the HIMARK™ Unstained HMW Protein Standard is supplied in a ready-to-use format. There is no need to heat or add reducing agent. The Standard is used as follows.

Thaw the standard at room temperature. Vortex gently to ensure the solution is homogeneous. Note that if there is a precipitate in the standard, thaw at room temperature for 10-15 minutes and vortex to solubilize or warm the solution at 30° C. (do not heat at >37° C.)

Best results are obtained when 5 µl of Standard are loaded on a 1.0 mm thick Mini-Gel, or 7 µl are loaded on a 1.5 mm thick Mini-Gel. Use an appropriate percentage of NUPAGE® NOVEX® Tris-Acetate Gel to resolve the proteins.

After electrophoresis, gels are stained with SILVERQUEST® Silver Staining Kit, SIMPLYBLUE™ SafeStain, or Coomassie protein stain. Avoid using SILVEREXPRESS® Silver Staining Kit.

When blotting gels, to obtain higher transfer efficiency during the transfer of high molecular weight proteins, avoid using methanol in the transfer buffer. After transfer, you may stain the standard proteins on the membrane with Ponceau S, Coomassie or any membrane stain of choice.

Note that the HIMARK™ Unstained HMW Protein Standard is designed for use with NUPAGE® NOVEX® Tris-Acetate Gels. Using the standards with NUPAGE® NOVEX® Bis-Tris Gels or Tris-Glycine Gels may result in inaccurate molecular weight estimation.

In one embodiment, the HIMARK™ Unstained High Molecular Weight Protein Standard is qualified on a NUPAGE® NOVEX® 3-8% Tris-Acetate Gel. After staining with Coomassie R-250 stain, 9 sharp protein bands of the appropriate molecular weight are observed.

A molecular weight calculator for use with HIMARK™ High Molecular Weight Protein Standard is available for downloading on the worldwide web at invitrogen.com by selecting the following links: Products & Services>Product Information>Life Science Products and Services>Electrophoresis>Protein Standards, Stains & Detection>Protein Standards>HIMARK™ Standard for large protein analysis (40-500 kDa). The calculator provides an tool to easily and accurately calculate the molecular weight of your proteins on NUPAGE® NOVEX® 3-8% and 7% Tris-Acetate Gels and to extrapolate the molecular weight of proteins beyond the standard curve.

Figure 5A:
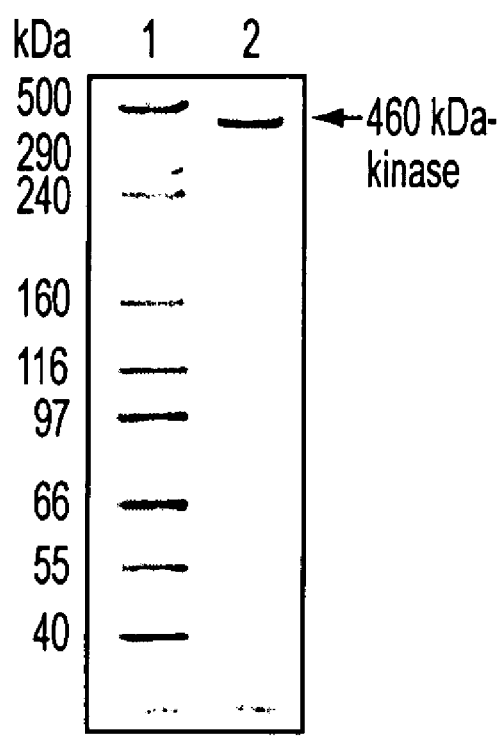
FIG. 5A shows results of electrophoretic experiments, i.e. an image of a 3-8% Tris-Acetate gel loaded with -HIMARK™ Pre-Stained Standard and a 460 kDa kinase.
Figure 5B:
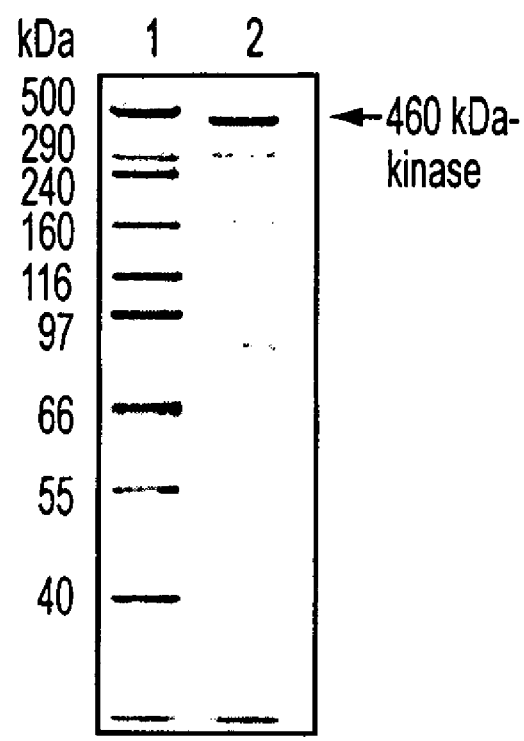
FIG. 5B shows an image of a 7% Tris-Acetate gel loaded with HIMARK™ Pre-Stained Standard and a 460 kDa kinase.
Figure 6:
FIG. 6 shows results of electrophoretic experiments, i.e. an image of a 3-8% Tris-Acetate gel that has been electrophoresed; lane 1, SEEBLUE® Plus2 Pre-Stained Standard; lane 2, HIMARK™ Pre-Stained Standard.
Figure 7:
FIG. 7 shows results of electrophoretic experiments, i.e. an image of a 7% Tris-Acetate gel that has been electrophoresed; lane 1, SEEBLUE® Plus2 Pre-Stained Standard; lane 2, HIMARK™ Pre-Stained Standard.
Figure 8:
FIG. 8 shows results of electrophoretic experiments, i.e. an image of a 4% Tris-Glycine gel that has been electrophoresed; lanes 1 and 2, HIMARK™ Pre-Stained Standard; lane 3, SEEBLUE® Plus2 Pre-Stained Standard.
Figure 9:
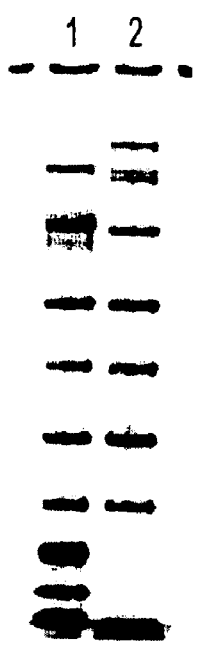
FIG. 9 shows results of electrophoretic experiments, i.e. an image of a 4-12% NUPAGE® gel that has been electrophoresed with 1×MES; lane 1, SEEBLUE® Plus2 Pre-Stained Standard; lane 2, HIMARK™ Pre-Stained Standard.

FIGS. 5A and 5B show Unstained HMW Protein Standard and a 460 kDa protein run on gels. Unstained HMW Protein Standard (5 µl) and a 460 kDa kinase were analyzed on a NUPAGE® NOVEX® 3-8% Tris-Acetate Gel (FIG. 5A) and a NUPAGE® NOVEX® 7% Tris-Acetate Gel (FIG. 5B), each of which is electrophoresed in the presence of Tris-Acetate SDS buffer and stained with Coomassie R-250 stain. The apparent molecular weights of protein standard bands are shown in FIGS. 5A and 5B. The arrow indicates the migration of a 460 kDa kinase.

Example 8

De-Phosphorylation

In order to make a phosphorylated protein population homogeneous, the protein is treated with kinase until the reaction is driven to completion to obtain a homogeneous population of phosphorylated proteins. Alternatively, a population of phosphorylated proteins is made homogeneous by dephosphorylation.

For example, for dephosphorylation, 100 µg of a phosphorylated or partially phosphorylated protein sample is solubilized in 100 µl 50 mM Tris/HCl, pH 7.5 containing 1 mM MgCl$_2$, and then incubated for about 10 min at 30° C. Then, from 20 to about 30 units of calf intestine alkaline phosphatase (CIAP) are added (CIAP is commercially available from a number of suppliers, including for example Stratagene, La Jolla, Calif., and Promega, Madison, Wis.). The mixture is incubated for about 15 minutes at about 30° C. The reaction is terminated by the addition of an equal volume of 2×SDS PAGE sample buffer and subsequent mixing. The sample is analyzed by SDS-PAGE to confirm that the reaction is complete, nearly complete, complete to an acceptable extent or complete to a detectable limit.

Example 9

DNA Methylation

DNA is prepared according to standard techniques and treated with a methylase, preferably a methylase that recognizes a specific nucleotide sequence, such as a methylase of a restriction system. After the methylation reaction, the solution comprising DNA is digested with the corresponding restriction enzyme to remove unmodified DNA molecules.

For example, a bacterial plasmid having a single EcoRI restriction site having the following structure is prepared, preferably in supercoiled form:

The plasmid DNA is treated with EcoRI Methylase (New England Biolabs, Beverly, Mass.) essentially according to the manufacturer's instructions. In brief, reactions are carried out in 50 mM NaCl, 50 mM Tris-HCl (pH 8.0), 10 mM EDTA, and 80 µM S-adenosylmethionine (SAM) is used as the methyl donor. The reactions are incubated at 37° C. Because EcoRI methylase is inhibited by MgCl$_2$, care is taken to avoid the addition of MgCl$_2$ to the methylation reaction.

Following the methylation reaction, most if not all of the plasmids have methyl residues to the EcoRI sites as indicated added as in the following structure:

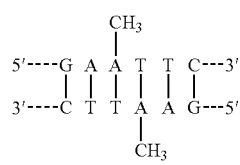

If need be, the resultant population of homogeneously methylated DNA is digested with restriction enzyme EcoRI (New England Biolabs), an endonuclease that cleaves the GAATTC sequence only if the above-described methylation has not taken place. The reaction is carried out using an appropriate buffer such as 50 mM NaCl, 100 mM Tris-HCl, 10 mM MgCl$_2$, 0.025% Triton X-100, pH 7.5). The reaction mixture is incubated at 37° C. The EcoRI enzyme is inactivated by heating at 65° C. for 20 minutes.

Digestion with the EcoRI endonuclease results in the linearization of the circular plasmid DNA. Methods for separating the undesired (unmethylated) linear DNA from the desired (methylated) circular plasmid DNA are known in the art and are used to further purify the methylated DNA from other species of DNA. For example, DNA prepared from a supercoiled plasmid is separated from linear DNA by ultracentrifugation in a cesium chloride gradient in the presence of ethidium bromide. The separated plasmid DNA is a population of a species of DNA molecule that is homogeneous, nearly homogeneous, homogeneous to a detectable limit, or homogeneous to a degree sufficient for the application.

The methylated circular DNA is then digested with a second restriction enzyme, which may have one or more sites on the plasmid, in order to generate a linear DNA standard, which may be molecular weight standard of the invention. The methylated plasmid can be one that comprises two or more sites for the second restriction enzyme; if these sites are not equidistant from each other, digestion of the plasmid with the second restriction enzyme will yield two molecular species of different sizes, each of which is a homogeneous population. In this procedure, two or more populations of homogeneous DNA molecules are prepared in a single tube.

Example 10

Pre-Stained Laminin

Deglycosylation, Reduction and Alkylation: Laminin is deglycosylated essentially according to the method of Example 2 except that concentration by centrifugation is performed at 1800×g rather than 3000×g. Laminin is then reduced and alkylated essentially according to the method of Example 3, with the exceptions that the initial room temperature incubation is for 1.5 hours, concentration by centrifugation is performed at 1800×g, and 100 mM AMPSO (pH 9) is used in place of 50 mM Tris (pH 8).

Staining: One ml of the 1 mg/ml deglycosylated, reduced and alkylated laminin solution, comprising 100 mM AMPSO (pH 9) and 1% SDS, is combined with 250 µl of 50 mg/ml Uniblue A in 20% SDS. The resulting sample is left on a shaker for 30 minutes to solubilize the Uniblue A, and then left 16-20 hours at 37° C. to stain.

Purification: The resulting pre-stained laminin is purified by gel filtration on TOYOPEARL® HM-40C resin (Tosoh Bioscience, Montgomeryville, Pa., USA) washed with 50 mM Tris (pH 8), 1% SDS. The same buffer solution (50 mM Tris (pH 8), 1% SDS) is used during purification.

Concentration: Purified pre-stained laminin is concentrated to 3 mg/ml using an Amicon 100 kDa MWCO filter, with caution not to exceed the 3 mg/ml target concentration.

Example 11

Pre-Stained β-Galactosidase

Alkylation: Alkylation is performed by mixing 1 ml of 1 mg/ml β-galactosidase, prepared in 50 mM Tris (pH 8) and 2% SDS, with 10 µl of 400 mM TBP in isopropyl alcohol. The sample is incubated at 70° C. for 20 minutes, 100 µl of 1 M iodoacetic acid pH 7 in 25 mM phosphate buffer is added. The sample is further incubated at 70° C. for 10 minutes and at room temperature for 30 minutes.

Purification: The alkylated β-galactosidase is dialyzed overnight against 100 mM AMPSO (pH 9), 1% SDS. The sample is dialyzed 3 more hours after the dialysis buffer is changed (i.e. the old 100 mM AMPSO (pH 9), 1% SDS is replaced with fresh).

Staining: Uniblue A (13 mg) is added to 1 ml of the purified alkylated P-galactosidase and the sample is incubated on a shaker for 1 hour at room temperature, and then at 47° C. for 16-20 hours.

Purification: The resulting pre-stained β-galactosidase is purified by gel filtration on TOYOPEARL® HM-40C resin washed with 50 mM Tris (pH 8), 1% SDS. The same buffer solution (50 mM Tris (pH 8), 1% SDS) is used during purification.

Concentration: Purified pre-stained β-galactosidase is concentrated to 2 mg/ml using an Amicon 50 kDa MWCO filter.

Example 12

HIMARK™ Pre-Stained Standards

Pre-stained laminin and pre-stained β-galactosidase, prepared as described in Examples 11 and 12, are mixed with other pre-stained proteins to provide a mixture of pre-stained markers covering a broad range of molecular weight. Pre-stained carbonic anhydrase, alcohol dehydrogenase, glutamic dehydrogenase and bovine serum albumin (MW) are components of SeeBlue® Pre-Stained Standards (Catalog No. LC5625, Invitrogen, Carlsbad, Calif., USA). The pre-stained proteins mentioned in this Example may be mixed together to form the HIMARK™ Pre-Stained Standard. The amounts of the various pre-stained proteins are adjusted to create a mixture where the intensities of bands for the various protein markers are substantially similar, or reflect some desired ratio of intensities. Once the HIMARK™ Pre-Stained Standard is created formamide sample buffer is added to 50% volume and it is stored at –20° C., at which temperature it does not freeze. Because the HIMARK™ Pre-Stained Standard is not frozen there is no delay caused by the need to thaw the standard before use, and the standard does not undergo repeated freeze-thaw cycling.

Such pre-stained high molecular weight markers provide many advantages. The progress of electrophoretic runs can be assessed in real time by observing the migration of pre-stained marker proteins as the run occurs, so that a user can end the run at the time when optimal resolution has been achieved. The progress and efficiency of western transfer onto a membrane can also be monitored to know when, and if, transfer is complete. HIMARK™ Pre-Stained Standard provides these advantages to experiments involving high molecular weight proteins. In addition, pre-stained markers do not require a staining or other detection step after the gel is run, potentially simplifying experiments.

FIGS. 6-22 illustrate the use of the HIMARK™ Pre-Stained Standard. FIGS. 6-9 illustrate the mobility of the HIMARK™ Pre-Stained Standard proteins in various commonly used gels for separation of large proteins, as well as the mobility of SEEBLUE® Plus2 Pre-Stained Standard proteins. Results are shown for 3-8% and 7% Tris-Acetate gels, a 4% Tris-Glycine gel and a 4-12% NUPAGE® NOVEX® gel run with 1×MES. Unless otherwise indicated, all standards in this Example are loaded at 10 µl/well.

Figure 10:
FIG. 10 shows results of electrophoretic and transfer experiments, i.e. an image of a 3-8% Tris-Acetate gel that has been electrophoresed, and the samples western transferred onto a nitrocellulose membrane; lane 1, HIMARK™ -Pre-Stained Standard; lane 2, SEEBLUE® Plus2 Pre-Stained Standard.
Figure 11:
FIG. 11 shows results of electrophoretic and transfer experiments, i.e. an image of a 7% Tris-Acetate gel that has been electrophoresed, and the samples western transferred onto a nitrocellulose membrane; lane 1, HIMARK™ -Pre-Stained Standard; lane 2, SEEBLUE® Plus2 Pre-Stained Standard.

FIGS. 10 and 11 illustrate the transfer of HIMARK™ Pre-Stained Standard proteins and SEEBLUE® Plus2 Pre-Stained Standard proteins to nitrocellulose membranes after electrophoresis.

Figure 12:
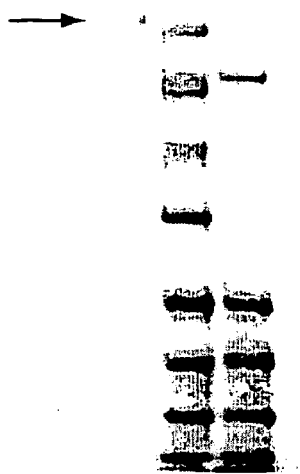
FIG. 12 shows results of electrophoretic, transfer and western blotting experiments, i.e. an image of an 8% Tris-Acetate gel that has been electrophoresed, western transferred onto a nitrocellulose membrane, and western blotted with specific polyclonal antibody to apolipoprotein B-100 from human plasma (referred to herein as "large human protein"); lane 1, large human protein (arrow); lane 2, HIMARK™ Pre-Stained Standard; lane 3, SEEBLUE® Plus2 Pre-Stained Standard.
Figure 13:
FIG. 13 shows results of electrophoretic, transfer and western blotting experiments, i.e. an image of an 8% Tris-Acetate gel that has been electrophoresed, western transferred onto a nitrocellulose membrane, and western blotted with anti-6× His antibody; lane 1, BENCHMARK™ Unstained Standard; lane 2, HIMARK™ Pre-Stained Standard; lane 3, SEEBLUE® Plus2 Pre-Stained Standard.

FIGS. 12 and 13 illustrate the detection of proteins by western blot. In FIG. 12, 300 ng of large human protein, HIMARK™ Pre-Stained Standard and SEEBLUE® Plus2 Pre-Stained Standard are run on a 3-8% Tris-Acetate gel and subsequently transferred to a nitrocellulose filter. Large human protein is detected using a specific polyclonal antibody. In FIG. 13, 5 µl of BENCHMARK™ Unstained Standard, HIMARK™ Pre-Stained Standard and SEEBLUE® Plus2 Pre-Stained Standard are run on a 7% Tris-Acetate gel and subsequently transferred to a nitrocellulose filter. BENCHMARK™ Unstained Standard is detected using an anti-6×His antibody.

Figure 14:
FIG. 14 shows results of electrophoretic and transfer experiments, i.e. an image of a 3-8% Tris-Acetate gel that has been electrophoresed, and the samples western transferred onto a PVDF membrane in the presence of 20% methanol and 1× Antioxidant (Catalog No. NP0005, Invitrogen, Carlsbad, Calif., USA); lane 1, HIMARK™ Pre-Stained Standard; lane 2, SEEBLUE® Plus2 Pre-Stained Standard.
Figure 15:
FIG. 15 shows results of electrophoretic and transfer experiments, i.e. an image of a 7% Tris-Acetate gel that has been electrophoresed, and the samples western transferred onto a PVDF membrane in the presence of 20% methanol and antioxidant; lane 1, HIMARK™ Pre-Stained Standard; lane 2, SEEBLUE® Plus2 Pre-Stained Standard.

FIGS. 14 and 15 show results for experiments similar to those of FIGS. 10 and 11, except that transfer is to PVDF rather than nitrocellulose membranes.

Figure 16:
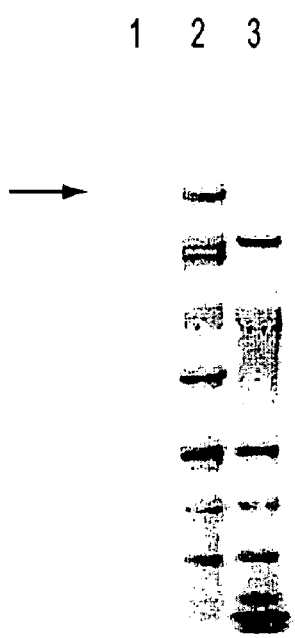
FIG. 16 shows results of electrophoretic, transfer and western blotting experiments, i.e. an image of a 3-8% Tris-Acetate gel that has been electrophoresed, western transferred onto a PVDF membrane, and western blotted with specific polyclonal antibody to large human protein; lane 1, large human protein (arrow); lane 2, HIMARK™ Pre-Stained Standard; lane 3, SEEBLUE® Plus2 Pre-Stained Standard.
Figure 17:
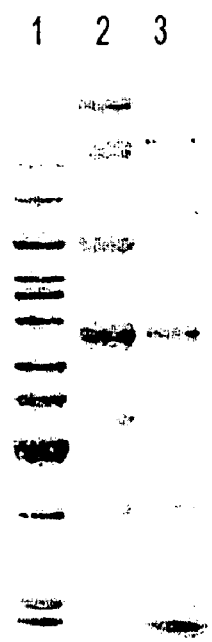
FIG. 17 shows results of electrophoretic, transfer and western blotting experiments, i.e. an image of a 7% Tris-Acetate gel that has been electrophoresed, western transferred onto a PVDF membrane, and western blotted with anti-6×His antibody; lane 1, BENCHMARK™ Unstained Standard; lane 2, HIMARK™ Pre-Stained Standard; lane 3, SEEBLUE® Plus2 Pre-Stained Standard.

FIGS. 16 and 17 show results for experiments similar to those of FIGS. 12 and 13, except that transfer is to PVDF rather than nitrocellulose membranes, and transfer is effected in the presence of 20% methanol and an antioxidant.

Figure 18:
FIG. 18 shows results of electrophoretic and transfer experiments, i.e. an image of a 4% Tris-Glycine gel that has been electrophoresed, and the samples western transferred onto a nitrocellulose membrane; lane 1, SEEBLUE® Plus2 Pre-Stained Standard; lane 2, HIMARK™ Pre-Stained Standard.
Figure 19:
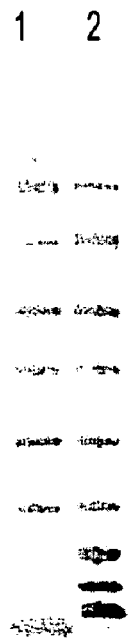
FIG. 19 shows results of electrophoretic and transfer experiments, i.e. an image of a 4-12% Bis-Tris gel run with MOPS that has been electrophoresed, and the samples western transferred onto a nitrocellulose membrane; lane 1, HIMARK™ Pre-Stained Standard; lane 2, SEEBLUE® Plus2 Pre-Stained Standard.

FIGS. 18 and 19 illustrate the transfer of HIMARK™ Pre-Stained Standard proteins and SEEBLUE® Plus2 Pre-Stained Standard proteins to nitrocellulose membranes after electrophoresis on a 4% Tris-Glycine gel or a 4-12% Bis-Tris gel run with MOPS, respectively.

Figure 20:
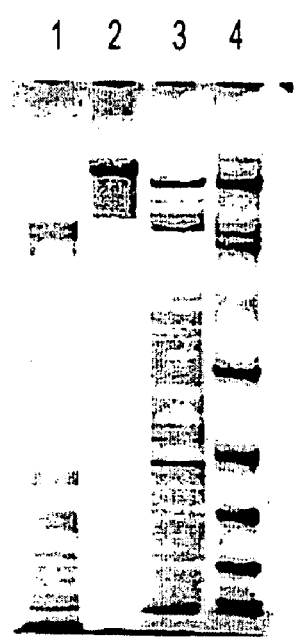
FIG. 20 shows results of electrophoretic experiments, i.e. an image of a 3-8% Tris-Acetate gel that has been electrophoresed and stained with SIMPLYBLUE™ Safe Stain; lane 1, fibronectin; lane 2, large human protein, lane 3, human kinase; lane 4, HIMARK™ Pre-Stained Standard.

FIG. 20 illustrates the use of HIMARK™ Pre-Stained Standard in a gel that is stained with SIMPLYBLUE™ Safe Stain. Protein samples, including, from left to right, fibronectin, large human protein, human kinase and HIMARK™ Pre-Stained Standard are run on a 3-8% Tris-Acetate gel and stained with SIMPLYBLUE™ Safe Stain.

Figure 21:
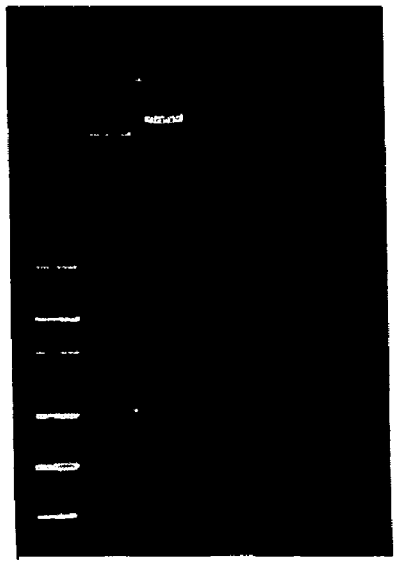
FIG. 21 shows results of electrophoretic experiments, i.e. an image of a 3-8% Tris-Acetate gel that has been electrophoresed and stained with SYPRO® Orange; lane 1, HIMARK™ Unstained Standard; lane 2, human kinase; lane 3, large human protein; lane 4, fibronectin; lane 5, HIMARK™ Pre-Stained Standard.
Figure 22:
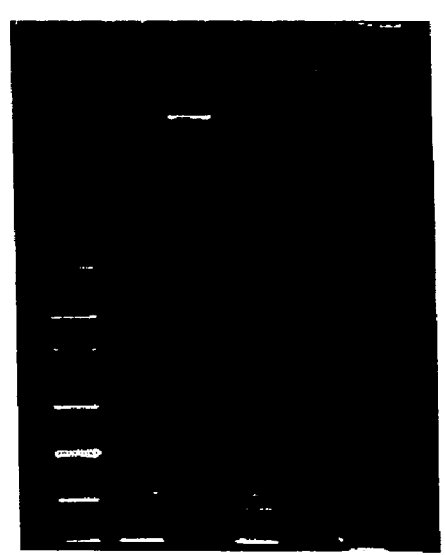
FIG. 22 shows results of electrophoretic experiments, i.e. an image of a 3-8% Tris-Acetate gel that has been electrophoresed and stained with SYPRO® Ruby; lane 1, HIMARK™ Unstained Standard; lane 2, human kinase; lane 3, large human protein; lane 4, fibronectin; lane 5, HIMARK™ Pre-Stained Standard. The number of ug of sample added in lanes 1-4 in FIG. 22 are 10% of that loaded in FIG. 21.

FIGS. 21 and 22 illustrate the use of HIMARK™ Pre-Stained Standard in gels that are stained with fluorescent dyes, i.e. SYPRO® Orange and SYPRO® Ruby (Molecular Probes, Eugene, Oreg., USA), respectively. HIMARK™ Pre-Stained Standard proteins appear as dark bands on the dark gray backgrounds in FIGS. 21 and 22. Such staining and detection methods may be particularly advantageous when gel electrophoresis of a sample is to be followed by additional procedures, such as mass spectrometry.

The invention illustratively described herein suitably may be practiced in the absence of any element or elements, limitation or limitations, which is not specifically disclosed herein. The terms and expressions that have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed herein, optional features, modification and variation of the concepts herein disclosed may be resorted to by those skilled in the art, and that such modifications and variations are considered to be within the scope of this invention as defined by the appended claims. In addition, where features or aspects of the invention are described in terms of Markush groups, those skilled in the art will recognize that the invention is also thereby described in terms of any individual member or subgroup of members of the Markush group. The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. Other aspects of the invention are within the following claims.

All publications, patents and patent applications mentioned in this specification are indicative of the level of skill of those skilled in the art to which this invention pertains, and are herein incorporated by reference in their entirety to the same extent as if each individual publication, patent or patent application was specifically and individually indicated to be incorporated by reference.

What is claimed is:

1. A method for estimating or determining an apparent or actual molecular weight of an uncharacterized molecule using a molecular weight standard set comprising at least two protein standards of known and different molecular weights, the method comprising:

a) separating by electrophoresis the uncharacterized molecule and at least one protein standard of the molecular weight standard set;

b) detecting the separated uncharacterized molecule and at least one separated protein standard of the molecular standard set; and c) comparing at least one separated protein standard of the molecular standard set to the separated uncharacterized molecule to estimate or determine the apparent or actual molecular weight of the uncharacterized molecule;

wherein at least one of the at least two protein standards is a high molecular weight protein standard having an apparent molecular weight of at least 250 kDa by SDS PAGE, wherein the high molecular weight protein standard is at least a partially homogeneous population of an isolated laminin polypeptide, wherein at least one post-translational modification has been removed from the isolated laminin polypeptide to produce the at least partially homogenous population of the isolated laminin polypeptide, and wherein the post-translational modification is selected from the group consisting of glycosylation and phosphorylation.

2. The method of claim 1, wherein at least two of the protein standards of the set are at least partially homogeneous populations of laminin polypeptides, wherein at least one post-translational modification that has been removed from the laminin polypeptides, wherein the post-translational modification is selected from the group consisting of glycosylation and phosphorylation.

* * * * *